US010994134B2

(12) United States Patent
Thor

(10) Patent No.: US 10,994,134 B2
(45) Date of Patent: May 4, 2021

(54) METHOD OF TREATING VOIDING DYSFUNCTION

(71) Applicant: Dignify Therapeutics, LLC, Research Triangle Park, NC (US)

(72) Inventor: Karl Bruce Thor, Cary, NC (US)

(73) Assignee: Dignify Therapeutics, LLC, Research Triangle Park, NC (US)

(*) Notice: Subject to any disclaimer, the term of this patent is extended or adjusted under 35 U.S.C. 154(b) by 0 days.

(21) Appl. No.: 16/741,968

(22) Filed: Jan. 14, 2020

(65) Prior Publication Data
US 2020/0222693 A1 Jul. 16, 2020

Related U.S. Application Data

(63) Continuation of application No. PCT/US2019/041170, filed on Jul. 10, 2019.
(Continued)

(51) Int. Cl.
*A61N 1/36* (2006.01)
*A61B 5/20* (2006.01)
(Continued)

(52) U.S. Cl.
CPC .......... *A61N 1/36007* (2013.01); *A61B 5/205* (2013.01); *A61N 1/0512* (2013.01); *A61N 1/0514* (2013.01)

(58) Field of Classification Search
CPC .............. A61N 1/36007; A61N 1/0512; A61N 1/0514; A61N 1/36; A61N 1/3606; A61N 1/36132; A61N 1/372; A61B 5/205
(Continued)

(56) References Cited

U.S. PATENT DOCUMENTS

| 5,744,474 A | 4/1998 | Thor |
| 7,047,078 B2 | 5/2006 | Boggs, II et al. |

(Continued)

FOREIGN PATENT DOCUMENTS

| WO | 2000025859 A1 | 5/2000 |
| WO | 2017021909 A1 | 2/2017 |
| WO | 2018039552 A1 | 3/2018 |

OTHER PUBLICATIONS

Bhadra et al., "High Frequency Electrical Conduction Block of the Pudendal Nerve", Journal of neural engineering, vol. 3, doi:10.1088/1741-2560/3/2/012., Jun. 2006, pp. 14.
(Continued)

*Primary Examiner* — Carl H Layno
*Assistant Examiner* — Anh-Khoa N Dinh
(74) *Attorney, Agent, or Firm* — Kevin E Flynn; Flynn IP Law

(57) ABSTRACT

A stimulator device for controlling waste storage for a subject, having one electrode placed in proximity to a portion of each of the right and left pudendal nerves, which contains efferent fibers that, when stimulated, produce contraction of the urethral or anal sphincter. The stimulator device having a pulse generator connected to electrodes, bilaterally, to provide stimulation for each electrode to stimulate pudendal efferent axons. The pulse generator adapted to provide a first type of stimulation to cause waste to be stored within the subject. The pulse generator adapted to provide a second type of stimulation, different from the first type of stimulation, to allow waste to be voided from the subject by blocking nerve impulses that accompany sphincter dyssynergia. An input device to allow an end user to select the first type of stimulation, the second type of stimulation, or no stimulation. Variations of the concept are disclosed.

34 Claims, 17 Drawing Sheets

Related U.S. Application Data

(60) Provisional application No. 62/696,578, filed on Jul. 11, 2018.

(51) Int. Cl.
*A61N 1/05* (2006.01)
*A61N 1/372* (2006.01)

(58) Field of Classification Search
USPC .......................... 606/29, 30, 31, 32; 607/41
See application file for complete search history.

(56) References Cited

U.S. PATENT DOCUMENTS

| | | | |
|---|---|---|---|
| 7,571,000 B2 | 8/2009 | Boggs, II | |
| 8,396,555 B2 | 3/2013 | Boggs, II et al. | |
| 9,072,886 B2 | 7/2015 | Gaunt | |
| 9,393,411 B2 | 7/2016 | Bhadra | |
| 9,446,245 B2 | 9/2016 | Grill et al. | |
| 9,623,243 B2 | 4/2017 | Chancellor | |
| 10,722,708 B2 | 7/2020 | Grill et al. | |
| 2003/0004553 A1* | 1/2003 | Grill | A61N 1/36007 607/40 |
| 2007/0255176 A1* | 11/2007 | Rondoni | A61B 5/204 600/573 |
| 2008/0242918 A1* | 10/2008 | Gross | A61N 1/36007 600/30 |
| 2009/0036945 A1* | 2/2009 | Chancellor | A61N 1/36175 607/39 |
| 2009/0054950 A1* | 2/2009 | Stephens | A61N 1/36007 607/41 |
| 2009/0254144 A1 | 10/2009 | Bhadra | |
| 2010/0094372 A1 | 4/2010 | Grill | |
| 2010/0240949 A1* | 9/2010 | Gerber | A61B 5/686 600/30 |
| 2013/0218229 A1 | 8/2013 | Sharma | |
| 2016/0129248 A1 | 5/2016 | Creasey | |

OTHER PUBLICATIONS

Cardenas et al., "Etiology and Incidence of Rehospitalization after Traumatic Spinal Cord Injury: A Multicenter Analysis", Arch Phys Med Rehabil, Nov. 2004, pp. 1757-1763, vol. 85.
Danuser et al., "Spinal 5-HT2 Receptor-Mediated Facilitation of Pudendal Nerve Reflexes in the Anaesthetized Cat", British Journal of Pharmacology, Jan. 3, 1996, pp. 150-154, vol. 118(1).
De Groat et al., "Plasticity in Reflex Pathways to the Lower Urinary Tract Following Spinal Cord Injury", Experimental neurology., May 2012, pp. 1-22, vol. 235(1).
Dumoulin et al., "Pelvic Floor Muscle Training Versus no Treatment, or Inactive Control Treatments, for Urinary Incontinence in Women: A Short Version Cochrane Systematic Review with meta-analysis", 2015, pp. 19, vol. 34(4).
Dumoulin et al., "Pelvic Floor Muscle Training Versus no Treatment, or Inactive Control Treatments, for Urinary Incontinence in Women", Cochrane Database of Systematic Reviews, Jan. 20, 2010, pp. 44, Issue 1.
Gaunt et al., "Transcutaneously Coupled, High-Frequency Electrical Stimulation of the Pudendal Nerve Blocks External Urethral Sphincter Contractions", Neurorehabilitation and Neural Repair, Jul./Aug. 2009, pp. 615-626, Vol. 23 No. 6.
Kessler et al., "Sacral Neuromodulation for Urinary Retention", Nature Clinical Practice Urology, Dec. 2008, pp. 657-666, vol. 5 No. 12.
Kilgore et al., "Reversible Nerve Conduction Block Using Kilohertz Frequency Alternating Current", Neuromodulation, Apr. 2014, pp. 242-255, vol. 17(3).
Ko et al., "Treatment of External Urethral Sphincter Hypertonicity by Pudendal Nerve Block Using Phenol Solution in Patients with Spinal Cord Injury", International Medical Society of Paraplegia, 1997, pp. 690-693, vol. 35.

Leippold et al., "Botulinum Toxin as a New Therapy Option for Voiding Disorders: Current State of the Art", European Urology, Apr. 18, 2003, pp. 165-174, vol. 44.
Maggi et al., "Neural Pathways and Pharmacological Modulation of Defecation Reflex in Rats", Gen. Pharmac.,1988, pp. 517-523, vol. 19(4).
Franciscus Maria Johannes Martens, "Diagnosis of Neurogenic Detrusor Overactivity and Treatment with Conditional Electrical Stimulation of the Dorsal Genital Nerves", Neurology and Urodynamics, 2011, pp. 18, vol. 30(4).
Gareth J. Sanger., "Chronic Constipation: Improved Understanding Offers a New Therapeutic Approach",The Journal of Physiology, 2016, pp. 4085-4087, vol. 594(15).
Peters et al., "Chronic Pudendal Neuromodulation: Expanding Available Treatment Options for Refractory Urologic Symptoms", Neurourology and Urodynamics, Sep. 28, 2009, pp. 1267-1271, vol. 29(7).
Peters et al., "Sacral Versus Pudendal Nerve Stimulation for Voiding Dysfunction: A Prospective, Single-Blinded, Randomized, Crossover Trial", Neurourology and Urodynamics, 2005, pp. 643-647, vol. 24.
Tai et al., "Block of External Urethral Sphincter Contraction by High Frequency Electrical Stimulation of Pudendal Nerve", The Journal of Urology, Nov. 2004, pp. 2069-2072, vol. 172(5).
Tai et al., "Bladder Inhibition or Voiding induced by Pudendal Nerve Stimulation in Chronic Spinal Cord Injured Cats", Neurourology and Urodynamics, Jul. 2007, pp. 570-577, vol. 26(4).
Tai et al., "Voiding Reflex in Chronic Spinal Cord Injured Cats Induced by Stimulating and Blocking Pudendal Nerves", Neurourol Urodynamics, Oct. 2007, pp. 879-886, vol. 26(6).
Thor et al., "Organization of Afferent and Efferent Pathways in the Pudendal Nerve of the Female Cat", The Journal of Comparative Neurology, Oct. 8, 1989, pp. 263-279, vol. 288(2).
Thor et al., "Neural Control of the Female Urethral and Anal Rhabdosphincters and Pelvic Floor Muscles", American journal of physiology Regulatory, integrative and comparative physiology, Aug. 2010, pp. R416-R438, vol. 299 (2).
Arnold Wald., "Diagnosis and Management of Fecal Incontinence", Current Gastroenterology Reports , Mar. 26, 2018, pp. 7, vol. 20(9).
Wang et al., "Bladder Inhibition or Excitation by Electrical Perianal Stimulation in a cat Model of Chronic Spinal Cord Injury", Journal Compilation © 2008 BJU International, Jun. 18, 2008, pp. 530-536, vol. 103, Issue 4.
Yoo et al., "Somatic Innervation of the Feline Lower Urinary Tract", Brain Research, Dec. 30, 2008, pp. 16, vol. 1246.
Zar-Kessler et al., "Botulinum Toxin Injection for Childhood Constipation is Safe and can be Effective Regardless of anal Sphincter Dynamics", Journal of Pediatric Surgery, Dec. 17, 2017, pp. 693-697, vol. 53.
Han, Inho, Patent Cooperation Treat International Search Report for International Application No. PCT/US2019/041170, dated Oct. 29, 2019, 7 pages, International Application Division of Korean Intellectual Property Office, Daejeon, Republic of Korea.
Han, Inho, PCT Written Opinion of the International Searching Authority for International Application No. PCT/US2019/041170, dated Oct. 29, 2019, 7 pages, International Application Division of Korean Intellectual Property Office, Daejeon, Republic of Korea.
Barber, Matthew D. et al., Innervation of the female levator ani muscles, Am J Obstet Gynecol, vol. 187, No. 1, Jul. 2002, pp. 64-71, Elsevier, New York, NY.
Bhadra, Niloy et al., High-Frequency Electrical Conduction Block of Mammalian Peripheral Motor Nerve, Muscle and Nerve, vol. 32, Dec. 2005, pp. 782-790, Wiley Periodicals, Hoboken, New Jersey.
FMJ Martens, Minimal invasive electrode implantation for conditional stimulation of the dorsal genital nerve in neurogenic detrusor overactivity, Spinal Cord, 2011, 566-572, vol. 49, International Spinal Cord Society, Aylesbury, United Kingdom.
Timothy J. Ness et al., Spinal Mechanisms of Pudendal Nerve Stimulation-Induced Inhibition of Bladder Hypersensitivity in Rats, Neuroscience Letters, Nov. 1, 2018, 181-185, vol. 686, Elsevier, Amsterdam, Netherlands.
Serge P. Marinkovic et al., Successful bilateral pudendal neuromodulation to treat male detrusor areflexia following severe pubic symphysis

(56) References Cited

OTHER PUBLICATIONS fracture, a case report, BMC Urology, 2015, 4 pages, (DOI 10.1186/s12894-015-0108-4), BioMed Central, London, United Kingdom.
Nucelio Lemos et al., Laparoscopic implantation of neuromodulators for treating urinary dysfunctions and improving locomotion in multiple sclerosis patients, International Urogynecological Journal, May 6, 2015 (online publication) (DOI 10.1007/s00192-015-2702-0), pp. 1871-1873, vol. 26, The International Urogynecological Association, Burnsville, Minnesota, USA.
Woock et al., "Activation and inhibition of the micturition reflex by penile afferents in the cat", Am J Physiol Regul Integr Comp Physiol., Jun. 2008, pp. R1880-R1889, vol. 294(6).
Chen et al., "Bilateral pudendal afferent stimulation improves bladder emptying in rats with urinary retention", BJU Int., Apr. 2012, pp. 1051-1058, vol. 109(7).
Hokanson et al., "State-dependent bioelectronic interface to control bladder function", Nature Scientific Reports Jan. 11, 2021, p. 314 vol. 11.
Yoo et al., "Bladder activation by selective stimulation of pudendal nerve afferents in the cat", Exp Neurol., Jul. 2008 pp. 218-225, vol. 212(1).
Rutter et al., "Detection of Bladder contraction from the Activity of the External Urethral Sphincter in Rats using sparse Regression", Trans Neural Syst Rehabil Eng., Aug. 2018, pp. 1636-1644, vol. (26)8.
Boggs et al., "Bladder emptying by intermittent electrical stimulation of the pudendal nerve", J. Neural Eng., Jan. 2006, pp. 43-51, vol. 3.
Grill et al., "Emerging clinical application of electrical stimulation: Opportunities for restoration of function", Journal of Rehab Research and Devel., Nov./Dec. 2001, pp. 641-653, vol. 38(6).
McGee et al., "Selective co-stimulation of pudendal afferents enhances bladder activation and improves voiding efficiency", Neurourol Urodyn., Nov. 2014, pp. 1272-1278, vol. 33(8), Publisher John Wiley & Sons Inc.
Wenzel et al.; "Detecting the onset of hyper-reflexive bladder contraction from pudendal nerve electrical activity", Trans Neural Syst Rehabil Eng., Sep. 2005, pp. 428-35, vol. 13(3).
Grill "Electrical stimulation for control of bladder function", Eng Med Biol Soc., 2009; pp. 2369-2370.
Yoo et al., "Minimally invasive electrical stimulation of the pudendal nerve: A pre-clinical study for Neural control of the lower Urinary tract", Neurourology and Urodynamics, 2007, pp. 562-569, vol. 26, Publisher John Wiley & Sons Inc.
Kennelly et al., "Electrical stimulation of the urethra evokes bladder contractions in a woman with spinal cord injury", J. Spinal Cord Med., Jun. 2010, pp. 261-265, vol. 33(3).
McGee et al., "Electrical stimulation for the treatment of lower urinary tract dysfunction after spinal cord injury", J Spinal Cord Medicine, 2015, 135-146, vol. 38(2), Publisher the Academy of Spinal cord injury Professionals. Inc.
Langdale et al., "Phasic activation of the external urethral sphincter increases voiding efficiency in the rat and the cat", Exp Neurol., Nov. 2016, pp. 173-181, vol. 285 (Pt B).
Boggs et al., "Frequency-dependent selection of reflexes by pudendal afferents in the cat", J Physiol., 2006, pp. 115-126, vol. 577(1).
McGee et al., "A spinal GABAergic mechanism is necessary for bladder inhibition by pudendal afferent stimulation", Am J Physiol Renal Physiol., 2014, pp. F921-F930, vol. 307(8).
Gustafson et al., "Fascicular anatomy and surgical access of the human pudendal nerve", World J Urol., 2005, pp. 411-418, vol. 23.
Peng et al., "Improved bladder emptying in urinary retention by electrical stimulation of pudendal afferents", J Neural Eng., Jun. 2008, pp. 144-154, vol. 5(2).

Woock et al., "Intraurethral stimulation evokes bladder responses via two distinct reflex pathways", J Urol., Jul. 2009, pp. 366-373, vol. 182(1), Publisher Elsevier.
Yoo et al., "Intraurethral activation of excitatory bladder reflexes in persons with spinal cord injury", Eng Med Biol Soc., 2009, pp. 6781-6784.
Woock et al., "Mechanisms of reflex bladder activation by pudendal afferents", Am J Physio Regul Integr Comp Physiol, 2011 pp. R398-R407, vol. 300.
McGee et al., Modeling the spinal pudendo-vesicai reflex for bladder control by pudendal afferent stimulation, J Comput Neurosci., Jun. 2016, pp. 283-296, vol. 40(3).
Kent et al., "Model-based analysis and design of nerve cuff electrodes for restoring bladder function by selective stimulation of the pudendal nerve", J Neural Eng., Jun. 2013, p. 036010, vol. 10(3).
Woock et al., "Finite element modeling and in vivo analysis of electrode configurations for selective stimulation of pudendal afferent fibers", BMC Urology, May 2010, vol. 10(11).
Gonzalez et al., "The Effects of neuromodulation in a novel obese-prone rat model of detrusor underactivity", Am J Physiol Renai Physiol., Jun. 2017, pp. F815-F825, vol. 313.
McGee et al., "Multiple Reflex pathways contribute to bladder activation by intraurethral stimulation in persons with spinal cord injury", Urology, Nov. 2017, pp. 210-215, vol. 109.
Yoo et al., "Multiple pudendal sensory pathways reflexly modulate bladder and urethral activity in persons with spinal cord injury", J Urol., Feb. 2011, pp. 737-743, vol. 185(2).
Gonzalez et al., "Sensory pudendal nerve stimulation increases bladder capacity through sympathetic mechanisms in cyclophosphamide-induced cystitis rats", Neurourol Urodyn., Jan. 2019; pp. 135-143, vol. 38(1), Publisher John Wley & Sons Inc.
Yoo et al., "Pudendal nerve stimulation evokes reflex bladder contractions in persons with chronic spinal cord injury", Neurourol Urodyn., 2007, pp. 1020-1023, vol. 26, Publisher Wiley-Liss, Inc.
Peng et al., "Role of pudendal afferents in voiding efficiency in the rat", Am J Physiol Regal integr Comp Physiol., Feb. 2008, pp. R660-R672, vol. 294(2).
McGee et al., "Selective co-stimulation of pudendal afferents enhances reflex bladder activation", Eng Med Biol Soc., 2011, pp. 1057-60.
Danziger et al., "Dynamics of the sensory response to urethral flow over multiple time scales in rat", J Physiol., 2015., pp. 3351-3371, vol. 593(15).
Yoo et al., "Somatic innervation of the feline lower urinary tract", Brain Res., Dec. 2008, pp. 80-87, vol. 1246.
Grill et al., "Identification of the spinal neural network involved in coordination of micturition in the male cat", Brain Research, 1998, pp. 150-160, vol. 796, Publisher Elsevier.
McGee et al., "Temporal pattern of stimulation modulates reflex bladder activation by pudendal nerve stimulation", Neurourol Urodyn., Nov. 2016, pp. 882-887, vol. 35(8), Publisher John Wiley & Sons Inc.
Hokanson et al., "Stimulation of the sensory pudendal nerve increases bladder capacity in the rat", Am J Physiol Renal Physiol., 2018, pp. F5430-F550, vol. 314.
Snelling et al., "Effects of stimulation site and stimulation parameters on bladder inhibition by electrical nerve stimulation", BJUI, 2012, pp. 136-43, vol. 110 (1).
Langdale et al., "Stimulation of the pelvic nerve increases bladder capacity in the PGE2 cat model of overactive bladder", Am J Physiol Renal Physiol., 2020, pp. F1357-1368, vol. 318.
Danziger et al., "Sensory feedback from the urethra evokes state-dependent lower urinary tract reflexes in rat", J Physiol., 2017, pp. 5687-5698, vol. 595(16).

\* cited by examiner

194

METHOD OF TREATING VOIDING DYSFUNCTION

This application is a continuation of co-pending and commonly assigned Patent Cooperation Treaty application No. PCT/US2019/041170 filed Jul. 10, 2019 for Method of Treating Voiding Dysfunction. The '170 application claims the benefit of then and commonly assigned U.S. Provisional Patent Application No. 62/696,578 filed on Jul. 11, 2018 for Method of Treating Voiding Dysfunction. This application claims the benefit of U.S. Provisional Patent Application No. 62/696,578 through the '170 application. The '170 application and the '578 application are both incorporated by reference in their entireties.

FIELD OF THE DISCLOSURE

This disclosure relates generally to methods to control micturition and defecation, as well as urinary and fecal continence, by stimulating nerves in animals, including humans.

BACKGROUND

Storage and Elimination of Urine.

The lower urinary tract (LUT) is responsible for the storage and periodic elimination of urine. Urine is stored in the urinary bladder, which serves as a urine reservoir, and is eliminated through the urethra, which serves as the urine outlet.

During the urine storage phase, the bladder must remain relaxed to allow it to stretch to accommodate increasing volumes of urine, while the urethra must remain closed to prevent leakage of urine (also termed urinary incontinence). Bladder relaxation is maintained by inhibition of bladder parasympathetic reflex pathways in the sacral spinal cord and by activation of efferent sympathetic axons in the hypogastric nerve and beta3 adrenergic receptor stimulation to induce bladder smooth muscle relaxation.

Urethral closure is maintained by both urethral smooth muscle contractions of the internal urethral sphincter that are promoted by the efferent sympathetic axons in the hypogastric nerve, through alpha1 adrenergic receptor stimulation to induce contraction, and by striated muscle contractions of the external urethral sphincter that are promoted by efferent somatic motor axons in the pudendal nerve through nicotinic cholinergic receptor activation.

As the bladder fills with increasing volumes of stored urine, stretch receptors in the bladder send signals along pelvic nerve afferent fibers to the sacral spinal cord, where they are relayed to lumbar sympathetic centers that in turn stimulate efferent sympathetic hypogastric nerve activity to further relax the bladder and contract the internal urethral sphincter. These bladder stretch receptors also activate the efferent somatic motor pudendal nerve activity to tighten the external urethral sphincter. Thus, relaxation of the bladder and contraction of urethral sphincters together promote urine storage as the bladder fills.

When the bladder is stretched to the point where voiding should occur, the bladder stretch receptors relay this sensory information to the brain, which suppresses the bladder sensations and sacral parasympathetic voiding reflexes, while promoting the urine storage reflexes. When it is behaviorally appropriate, the brain inhibits the sympathetic and somatic urine storage reflexes to allow relaxation of the urethral sphincters and activates the sacral parasympathetic micturition reflex to produce a bladder contraction of sufficient strength and duration to completely empty the bladder. Thus, relaxation of the urethra and contraction of the bladder together produce efficient urine voiding. Urine voiding is sometimes called micturition or urination.

Storage and Elimination of Feces.

Similar to the storage and elimination of urine by LUT, the lower gastrointestinal (GI) tract is responsible for the storage and periodic elimination of feces (also termed stools). Feces are stored in the descending and sigmoid colon, which serves as a fecal reservoir, and are eliminated through the rectum and anus, which serves as the fecal outlet.

During the fecal storage phase, the descending and sigmoid colon must remain relaxed to allow stretch to accommodate increasing volumes of feces, while the rectum maintains tone to detect entry of feces, and the anus is closed to prevent leakage of feces (also termed fecal incontinence). Descending and sigmoid colon relaxation is maintained by activity of efferent sympathetic axons in the hypogastric nerve and alpha2 adrenergic receptor activation that inhibits GI smooth muscle. Anal closure is maintained by both smooth muscle contractions promoted by the efferent sympathetic axons in the hypogastric nerve through alpha1 adrenergic receptors and by striated muscle contractions of the external anal sphincter promoted by efferent somatic motor axons in the pudendal nerve through nicotinic cholinergic receptors. As the descending and sigmoid colon fill with increasing volumes of feces, stretch receptors send signals through intrinsic and extrinsic GI reflex pathways to tighten the smooth and striated muscle of the external anal sphincter, as well as inhibit sacral parasympathetic defecation reflex pathways.

As feces are propelled into the descending and sigmoid colon via peristalsis, the rectum begins to stretch, which inhibits peristalsis in the descending colon and contracts the rectum and anal sphincters. As the rectum is stretched to the point where voiding (also termed defecation) should occur, the rectal stretch receptors relay this sensory information to the brain, which can suppress the rectal sensations and the sacral parasympathetic defecation reflexes, while promoting the colon storage reflexes, until defecation is appropriate. When defecation is appropriate, the sacral parasympathetic defecation reflex is activated to relax the striated external anal sphincter, contract the sigmoid colon, and propel feces into the rectum, which simultaneously relaxes and stretches as it accepts the feces. The rectal stretching activates the rectoanal inhibitory reflex that relaxes the smooth muscle of the internal anal sphincter. Thus, contraction of the sigmoid colon coordinated with relaxation of the anal sphincters produces efficient defecation.

Continence and Voiding.

Healthy bladder and GI voiding behavior can thus be considered to exist in two modes: (1) continence or "storage mode" when the bladder and colon are relaxed and the external urethral and anal sphincters are contracted and (2) "voiding mode" when the bladder or colon contract and the external urethral and anal sphincters relax.

Incontinence.

Urinary and fecal incontinence are the involuntary loss of urine or feces, respectively, and can be caused by dysfunction of either the voiding or storage reflexes or both. Stress incontinence, which is an involuntary loss of urine or feces upon physical exertion (e.g. sporting activities or laughing, sneezing or coughing), is considered a weakness in storage reflexes and sphincter function, especially among women. Urge incontinence, which is an involuntary loss of urine or feces associated with episodic bladder or colon contractions and/or sensations of urgency, is considered an overactivity of the voiding reflexes. Some individuals are diagnosed with mixed incontinence, which is a combination of stress and urge urinary or fecal incontinence. Such urinary and fecal incontinence affects quality of life and participation in social and professional activities.

Dysfunctional Retention of Urine or Feces.

Urinary and fecal retention are the inability to efficiently void urine or feces, respectively, and can be caused by dysfunction of either the voiding or storage reflexes or both. Dysfunctional voiding reflexes cannot produce contractions of the bladder or colon that are of sufficient strength or duration to completely empty the bladder or colon of urine or feces, respectively. Dysfunctional storage reflexes can produce contractions of the urethral and anal sphincters that prevent the passage of urine or feces, respectively, when micturition or defecation are desired. This lack of coordination between bladder or colon contraction on one hand, and urethral or anal sphincter relaxation on the other hand, is termed sphincter dyssynergia. Thus, dysfunctions of either voiding or storage reflexes can result in residual urine in the bladder and feces remaining in the colon, respectively. Residual urine in the bladder can cause renal damage and promote urinary tract infections, either of which can be life-threatening. Feces remaining in the sigmoid colon can promote fecal impaction and functional constipation.

Impaired Nervous Systems.

Many individuals with damage or disease of the nervous system (e.g. spinal cord injury (SCI), spina bifida, multiple sclerosis) exhibit conditions of both incontinence and retention of both urine and feces (i.e. urinary incontinence and urinary retention and/or fecal incontinence and fecal retention). In this population, for example, the bladder contracts involuntarily, producing "uninhibited, neurogenic, non-voiding, bladder contractions" that overcome urethral resistance to cause urinary incontinence, but they also exhibit bladder-sphincter dyssynergia that produces urinary retention. Because the brain can no longer control and coordinate voiding or storage reflexes, the bladder and colon do not contract and empty properly to prevent retention, and the sphincters do not contract properly to prevent incontinence. Similar co-morbid voiding dysfunction is also prevalent in diabetics with diabetic cystopathy and gastroenteropathy and in community-dwelling and institutionalized elderly individuals.

Urinary Retention Treatment.

Urinary retention in SCI individuals is such a severe and unique condition that treatments, considered to be inappropriately risky for the general population, are used, but with limited success.

Current therapies for eliminating sphincter dyssynergia (Leippold et al., 2003 Eur Urol. August; 44(2):165-74) are intraurethral injection of botulinum toxin or surgical sphincterotomy, which produce semi-permanent or permanent paralysis of the sphincter, respectively. Naturally, paralysis of the sphincter prevents it from functioning and exacerbates involuntary leakage of urine (urinary incontinence) throughout the day. Another approach to drain urine from the bladder is catheterization. Some patients require an indwelling catheter to be inserted into the bladder through the urethra or a suprapubic incision, allowing one to continuously drain urine into a collecting bag attached to the patient's leg. Other patients use intermittent bladder catheterization, which requires passage of a catheter through the urethra into the bladder multiple times per day for the rest of the patient's life. Intermittent catheterization is obviously inconvenient and difficult or impossible (for quadriplegics) without caregiver assistance. Both forms of catheterization are also a major cause of catheter-associated urinary tract infections (CAUTIs) that result in hospitalization of 1 of 16 SCI individuals each year. The medical costs associated with urinary tract-related hospitalization are estimated at more than $12,000/year/patient and a total U.S. healthcare cost of $300-400 MM/year (Cardenas et al 2004 Archives Physical Medicine and Rehabilitation 85:1757-1763; DeVivo and Farris 2011 Top Spinal Cord Inj Rehabil, 16:53-61). The number of SCI individuals in the U.S. today exceeds 270,000 (National Spinal Cord Injury Statistical Center, Birmingham, Ala., 2013). Therefore, there is a great medical need for a safe and efficacious therapy that can block sphincter dyssynergia to eliminate or reduce the need for sphincterotomy, botulinum toxin injections, and/or catheterization.

Not only do SCI individuals have voiding difficulty due to sphincter dyssynergia and weak bladder contractions, they also have urine storage difficulty or urinary incontinence due to intermittent relaxations of the sphincter during uninhibited neurogenic bladder contractions. Acute SCI results in an 'areflexic' bladder in which urine builds up without any sensation of filling or physical ability to void. With time, involuntary, spinally-organized, bladder reflexes develop (de Groat and Yoshimura, 2012 Exp Neurol 235:123-132). Unfortunately, these spinal reflexes only produce weak (but frequent), short-duration, neurogenic, bladder contractions that do not empty the bladder but instead cause leakage of small amounts of urine throughout the day, i.e. urinary incontinence. Thus, most people with SCI have both urinary incontinence and retention.

Studies by Ko and Kim (1997 Spinal Cord. October 35(10):690-3) demonstrated that injecting phenol into the pudendal (PUD) nerve resulted in the relaxation of the sphincter with subsequent increases in voiding efficiency. However, phenolic poisoning of the pudendal nerve results in permanent loss of sphincter activity, which promotes incontinence, and thus does not solve the goal of temporary and reversible control of the pudendal nerve.

None of the above treatments for SCI individuals are appropriate for stress, urge or mixed incontinence in the general population. Currently, the only treatment available in the United States for which there is good evidence of effectiveness is pelvic floor muscle training, and it is considered first-line treatment for stress incontinence and mixed incontinence (Dumoulin and Hay-Smith 2010 Cochrane Database Syst Rev. January 20; (1):CD005654). Antimuscarinic agents and beta3 receptor antagonists can be used for urge incontinence.

In men who have undergone radical prostatectomy, which damages the urethral sphincter, an artificial urinary sphincter may be surgically implanted. However, these are reserved only for the most severe cases, because they produce ischemia and urethral erosion with time.

Sacral nerve stimulation is moderately effective for treatment of urge incontinence and fecal incontinence in patients with intact spinal cords, while tibial nerve stimulations, anal injections of bulking agents, and radio frequency energy have shown modest, but clinically significant, reductions in fecal incontinence (Wald A; Curr Gastroenterol Rep. 2018 Mar. 26; 20(3):9).

Cases of urinary retention are seen, rarely, in women with Fowler's syndrome and in children due to an inability to relax the pelvic floor and sphincters. In women, sacral nerve stimulation has been used with success (Kessler and Fowler 2008 Nat Clin Pract Urol. December 5(12):657-66). In both women and children, pelvic floor biofeedback training has also been attempted.

Fecal Retention Treatment.

Diet, enemas, and manual extraction are currently the primary methods of controlling fecal retention. Anal sphincter injections of botulinum toxin have also been reported as treatment of fecal retention in children (Zar-Kessler et al., 2018 J Pediatr Surg. April; 53(4): 693-697).

There have been attempts to control urethral sphincter dyssynergia using electrical stimuli. Preclinical studies in anesthetized cats (Bhadra et al. 2006 J Neural Eng. June 3(2):180-7; Gaunt et al., 2008 Neurorehabil Neural Repair. 2009 Jul.-Aug. 23(6):615-26; Wang et al., 2009 BJU Int. February 103(4):530-6; reviewed in Kilgore and Bhadra, 2014) showed that blockade of the pudendal nerve is highly effective in relaxing the urethral sphincter and improving voiding (Tai et al. 2004 J Urol. November 172(5 Pt 1):2069-72, Bhadra et al. 2006 J Neural Eng. June 3(2):180-7, Kilgore and Bhadra, 2014). Temporarily blocking amputee nerve pain and back nerve pain by using high frequency (e.g. 5-20 kHz) stimulation is known in the art (Kilgore and Bhadra, 2014 Neuromodulation. April 17(3):242-54). There have been no previous reports of using such high frequency stimulation in humans to block the pudendal nerve.

In U.S. Pat. No. 9,623,243 (Chancellor and Tai), one implanted electrode is used to excite the pudendal nerve to contract the bladder while second and optionally third electrodes are used to block the pudendal to external urethral sphincter conduction to prevent external urethral sphincter contraction.

In U.S. Patent Publication 2016/0129248 (Creasey and Toong), a dermal patch is applied over the dorsal nerve in order to send electrical signals that will control contraction and relaxation of the bladder.

In U.S. Pat. Nos. 8,396,555; 7,047,078; and 7,571,000; Boggs et al. describe the use of electrodes placed in a targeted region of the pudendal nerve to stimulate afferent fibers to evoke bladder contractions with one selected frequency while applying a second selected frequency range to inhibit bladder contractions.

In U.S. Pat. No. 9,072,866, Gaunt and Prochazka describe blocking of the pudendal nerve by stimulation with high frequency electrical pulses which cause the urethral sphincter to open, allowing bladder voiding. The pudendal nerve is blocked to allow bladder voiding until the bladder is empty.

In U.S. Pat. No. 9,393,411, Bhadra et al. describe a method for bladder control involving a first electrode coupled to an afferent nerve to which is applied a stimulation to reduce contractions of the urethral sphincter and a second electrode coupled to an afferent or efferent nerve to which is applied a second pulse burst stimulation to stimulate contractions of the bladder, which together result in complete voiding of the bladder.

Incontinence results from overactivity of the bladder and colon on one hand and/or underactivity of the urethral and anal sphincters on the other hand. Urinary and fecal retention result from underactivity of the bladder and colon on one hand and/or overactivity of the urethral and anal sphincters (sphincter dyssynergia) on the other hand. Therefore, therapy that increases the activity of the urethral and anal sphincters during storage of urine and feces, and blocks activity of the urethral and anal sphincters during voiding of urine and feces, is desired.

Vocabulary.

Cystometry is a clinical diagnostic procedure used to evaluate bladder function. Specifically, it measures contractile force of the bladder when voiding. See: //en.wikipedia.org/wiki/Cystometry. A cystometrogram (CMG) is a physiograph tracing resulting from cystometry procedures.

Bladder capacity (BC) refers to the volume of fluid that can be held in the bladder without voiding or leaking.

Bladder leak point pressure (LPP) is the pressure at which fluid leaks from the bladder and through the urethra in the absence of a bladder contraction.

Bladder voiding pressure (BVP) is the pressure at which fluid is expelled from the bladder through the urethra during a bladder contraction.

Electromyography (EMG) is a measurement of the electrical activity of a muscle, for example the striated anal or urethral sphincter muscle.

Pressure measurements are frequently made with respect to a column of a fluid. Two common fluids used for this purpose are mercury (Hg) and water (H20). As mercury is denser than water, a particular pressure will support a taller column of H2O than Hg. One millimeter of Hg is thus equal to 1.35951 centimeters of H20.

A stimulus response curve examines the effect of incrementally increasing the current, pulse duration, or frequency of the stimulus pulse while monitoring the relative changes in urethral, anal, or bladder pressure response.

A threshold response is the minimal current (I-T) or pulse width (PW-T) required to evoke a contraction of the external urethral or external anal sphincter, while a maximal response is the response that occurs at a given current (I-max) or pulse width (PW-max) above which no further increases in current or pulse width produce further increases in the contraction response of the external urethral or external anal sphincters.

Afferent neurons and efferent neurons are well-known in the art. Within the brain itself, the designation of afferent and efferent is context based but that is not relevant here. Within this disclosure, afferent neurons carry sensory information from peripheral organs as nerve impulses towards a central organ such as the brain or spinal cord. Afferent neurons are sometimes called sensory neurons. Efferent neurons transmit nerve impulses from the brain or spinal cord to the periphery of the body, such as to muscles and other structures. Efferent neurons are sometimes called motor neurons.

Unless explicit to the contrary, the word "or" should be interpreted as an inclusive or rather than an exclusive or. Thus, the default meaning of or should be the same as the more awkward and/or.

Unless explicit to the contrary, the word "set" should be interpreted as a group of one or more items.

Unless explicitly indicated as the smooth or internal urethral sphincter, the phrase "urethral sphincter" should be interpreted as the striated, external urethral sphincter.

Unless explicitly indicated as the smooth or internal anal sphincter, the phrase "anal sphincter" should be interpreted as the striated, external anal sphincter.

Frequently, when describing an industrial process it is useful to note that a given parameter is substantially met. Examples may be substantially parallel, substantially perpendicular, substantially uniform, and substantially flat. In this context, substantially X means that for purposes of this industrial process it is X. So something that may not be absolutely parallel but is for all practical purposes parallel is substantially parallel. Likewise, mixed air that has substantially uniform temperature would have temperature deviations that were inconsequential for that industrial process.

As recognized in C. E. Equipment Co. v. United States, 13 U.S.P.Q.2d 1363, 1368 (Cl. Ct. 1989), the word "substantially" in patent claims gives rise to some definitional leeway—thus the word "substantially" may prevent avoidance of infringement by minor changes that do not affect the results sought to be accomplished.

The term "about" means that quantities, parameters, shapes and other characteristics are not and need not be exact, but may be approximate and thus larger or smaller, reflecting tolerances, conversion factors, rounding off, measurement error and the like, and other factors known to those of skill in the art. In general, a quantity or characteristic is "about" or "approximate" whether or not expressly stated to be such.

Furthermore, the transitional terms "comprising", "consisting essentially of" and "consisting of", when used in the appended claims, in original and amended form, define the claim scope with respect to what un-recited additional claim elements or steps, if any, are excluded from the scope of the claim(s). The term "comprising" is intended to be inclusive or open-ended and does not exclude any additional, un-recited element, method, step or material. The term "consisting of" excludes any element, step or material other than those specified in the claim. The term "consisting essentially of" limits the scope of a claim to the specified elements, steps or material(s) and those that do not materially affect the basic and novel characteristic(s) of the claimed invention.

The term patient is most often a reference to a human that would benefit from a stimulating device in accordance to the teachings of this disclosure. The term patient should be read expansively to include animals that have received a stimulating device. The term patient also includes a teaching simulator that receives a stimulating device and is used by medical or veterinarian, or research personnel.

End user may be a set of people that includes the patient (having the one or more electrodes providing stimulus to the pudendal nerve). The term end user includes caregivers such as nurses or other professionals providing care to the patient and family members that may assist with providing care.

SUMMARY OF THE DISCLOSURE

This disclosure describes devices and methods that will allow individuals to voluntarily control when and where they void by using control pulses to the pudendal nerve, delivery of said pulses being under the control of the individual or the individual's caregivers. The control pulses may be electrical or magnetic. The use of these devices and methods eliminates or reduces urinary and fecal incontinence episodes and eliminates or reduces the need for catheterization of the bladder and manual extraction of feces that is a result of sphincter dyssynergia. Stimulation of the pudendal nerve efferently, and afferently, is accomplished via a single electrode to both contract the external urethral sphincter and external anal sphincter, and relax the bladder and colon, respectively, in order to provide a "storage mode" control, in addition to using the same electrode or magnetic coil, via a switch, to provide signals for a "voiding mode" to allow the bladder and colon to fully void by relaxing the external urethral and anal sphincters while contracting the bladder or colon physiologically, pharmacologically, or electrically. As noted below, optionally the stimulus for the storage mode and the voiding mode does not have to come from the same electrode or magnetic coil.

Aspects of the teachings contained within this disclosure are addressed in the claims submitted with this application upon filing. Rather than adding redundant restatements of the contents of all of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

It is intended herein that particular features (for example integers, characteristics, values, uses, diseases, disorders) described in conjunction with a particular aspect, embodiment or example of the invention are to be understood as applicable to any other aspect, embodiment or example described herein unless incompatible therewith. All of the features disclosed herein, including the steps of any method or components of any devices, may be combined in any combination, except combinations where at least some of the features or components are mutually exclusive. The invention is not restricted to any details of any disclosed embodiments. The invention extends to any one or any combination of the features disclosed herein, or to any one or any combination of the steps of any method or device components so disclosed.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Balancing Simplicity for Sake of Clarity and Precision.

Figure 1:
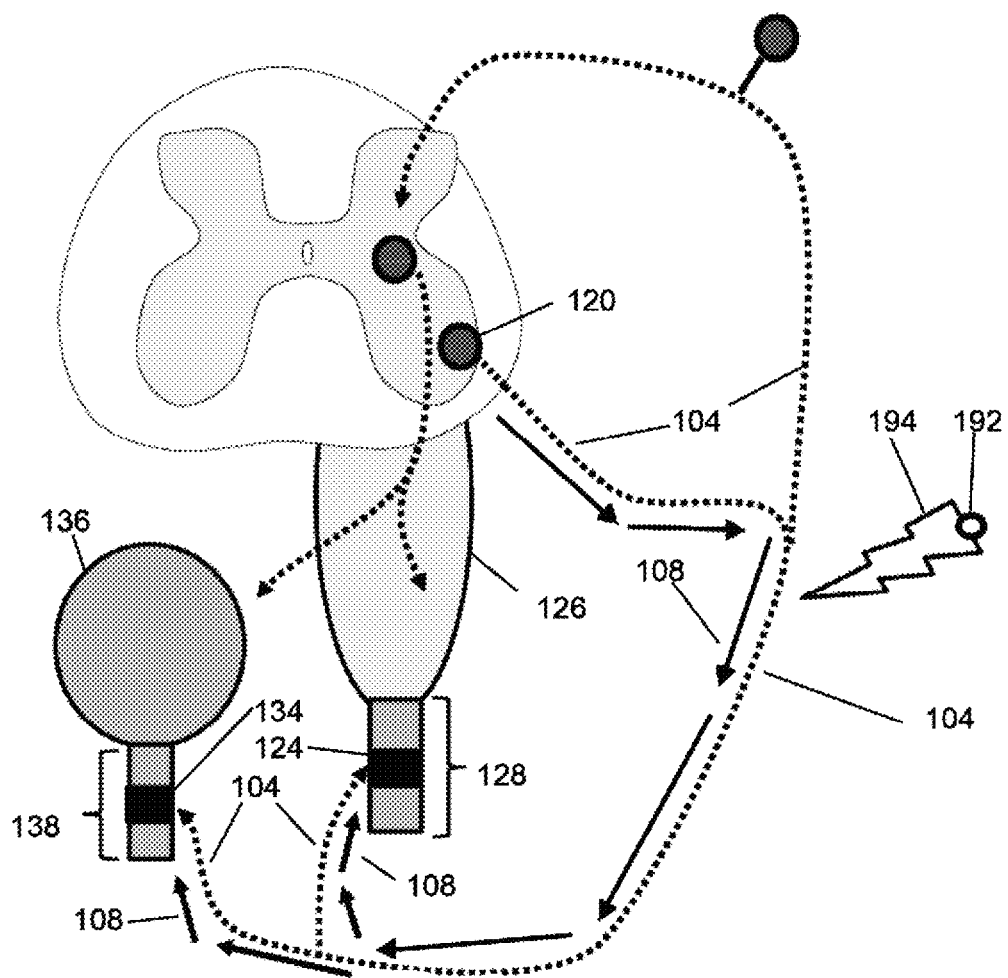
FIG. 1 is a schematic diagram showing placement of electrode within electrical stimulation range of the pudendal nerve and the action to use Low Frequency Stimulation to contract the external anal sphincter and the external urethral sphincter.
Figure 2:
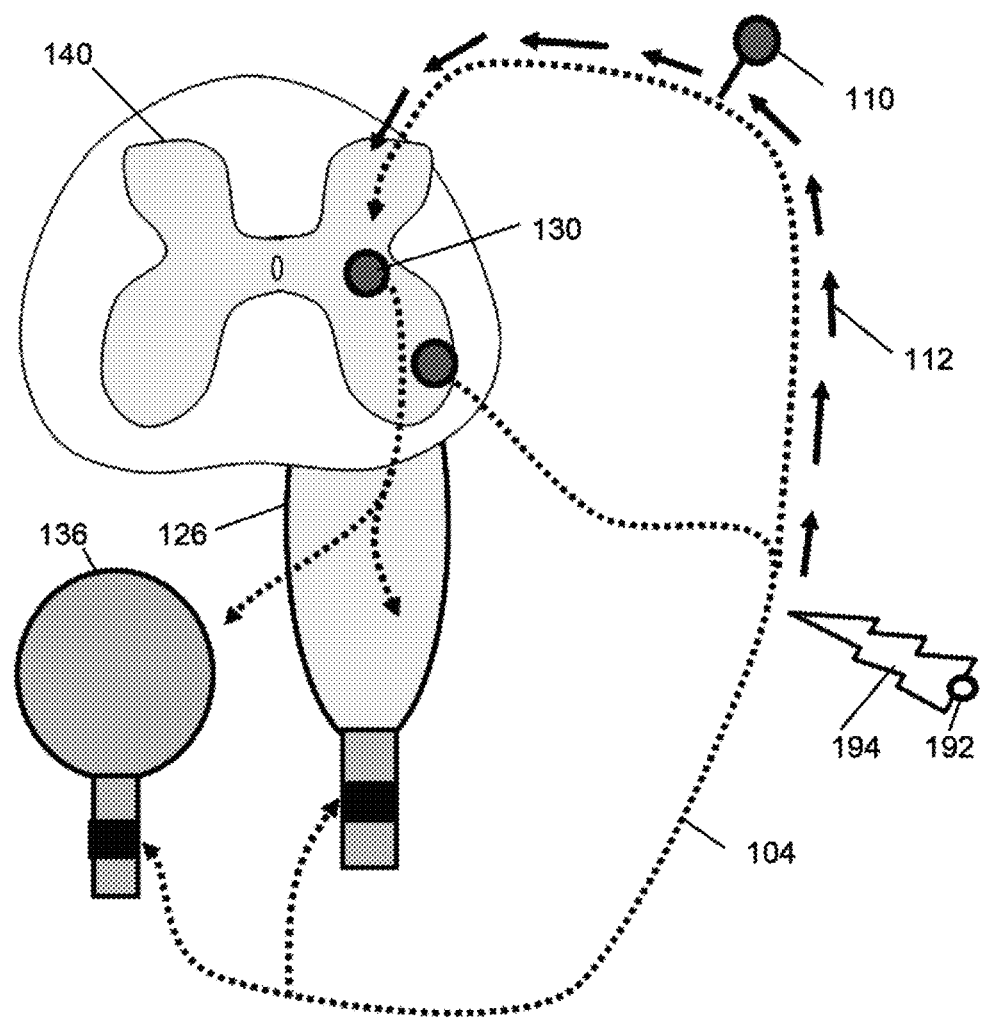
FIG. 2 shows the use of Low Frequency Stimulation to inhibit or excite the bladder/GI spinal cord neuron to relax or excite the bladder/colon.
Figure 3:
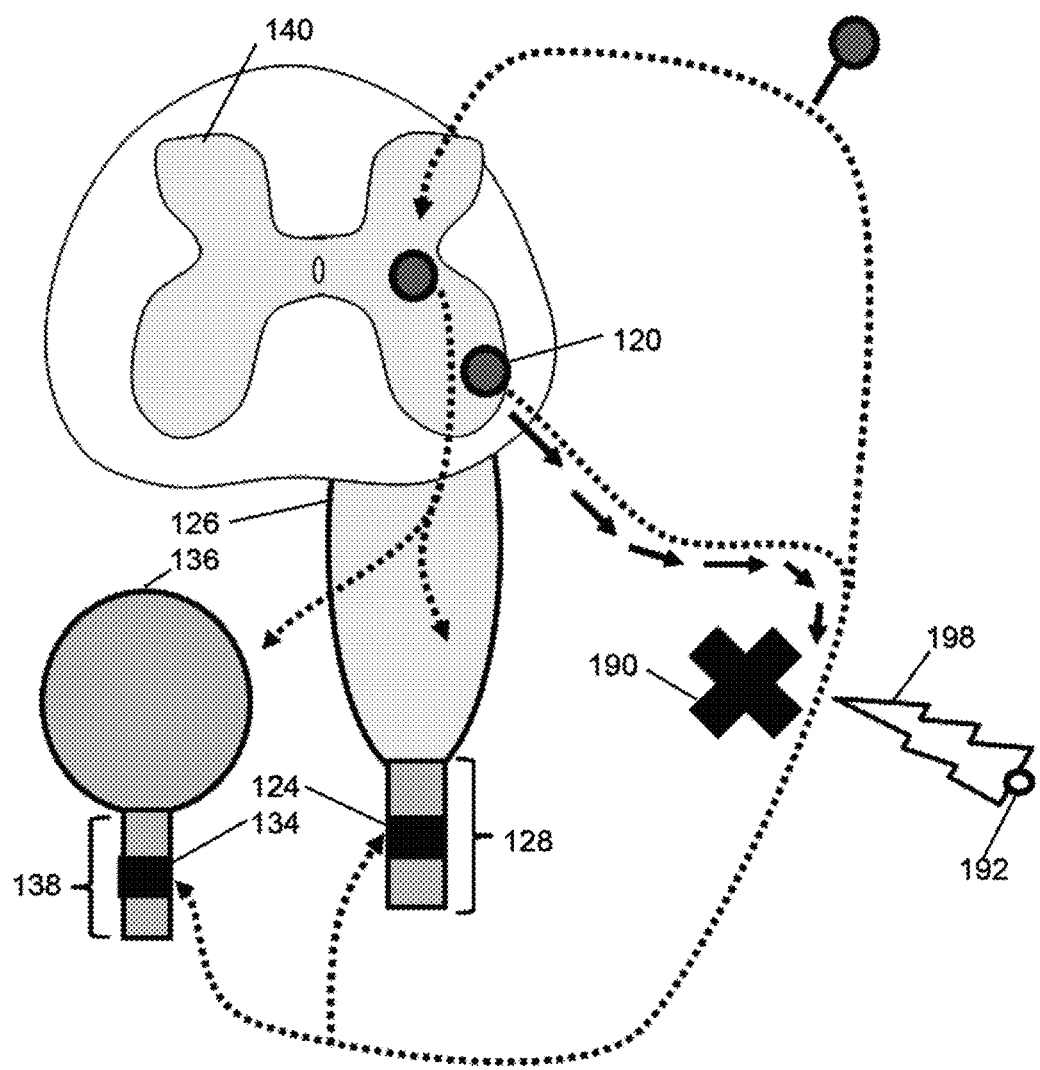
FIG. 3 shows the use of High Frequency Stimulation to block physiologically generated action potentials from sphincter efferent motor neurons in order to keep the external anal sphincter and the external urethral sphincter relaxed and open.

One of skill in the art will recognize that FIG. 1, FIG. 2, and FIG. 3 while potentially helpful illustrations for the present disclosure are symbolic representations and not a detailed representation of the relevant anatomy. For example, these figures do not seek to represent things to scale. For clarity, the following elements are introduced here before the detailed discussion:

104—Pudendal Nerve. This nerve contains both afferent axons and efferent axons which are discussed individually as part of this disclosure.

120—Sphincter Motor Neurons (as noted—Motor Neurons are also called Efferent Neurons) which provide the efferent axons to the pudendal nerve 104 and ultimately to the external urethral sphincter 134 and the external anal sphincter 124.

110—Afferent Neurons (sometimes called sensory neurons) have afferent axons in the pudendal nerve 104 to receive sensory input.

Low Frequency Stimulation (LFS).

FIG. 1 is a schematic diagram showing placement of electrode 192 within electrical stimulation range of the pudendal nerve 104 to deliver low frequency stimulation (LFS) 194 to the pudendal nerve 104 which produces action potentials (direction of action potential propagation depicted by arrows 108) in the pudendal nerve sphincter efferent neurons' axons to produce contraction of the sphincters. More specifically, the LFS 194 of the sphincter efferent neurons' 120 axons carried in branches of the pudendal nerve 104 substantially closes the external urethral sphincter 134 in the urethra 138 to seal the bladder 136. The LFS 194 causes contraction of the external anal sphincter 124 to substantially seal the anal canal 128 and thus seal the colon 126.

FIG. 2 diagrams a second impact of LFS 194 when stimulating the pudendal nerve 104.

The LFS 194 causes stimulation of the pudendal afferent neurons' 110 axons that also produces action potentials (direction of action potential propagation depicted by arrows 112) that are relayed to the sacral spinal cord 140. If the stimulation frequency is between 1-10 Hz, the dominant effect is to substantially inhibit the bladder/GI efferent neuron 130 and produce relaxation of the bladder 136 and possibly the colon 126. If the frequency of stimulation is 20-33 Hz, the dominant effect is to substantially excite the bladder/GI efferent neuron 130 and produce contractions of the bladder 136 and possibly colon 126. Between 10 and 20 Hz mixed effects might be obtained based on individual variability; one practiced in the art would make an empirical decision whether the benefit of increased frequency to produce more robust contraction of the sphincter provides sufficient benefit to counteract the loss of bladder inhibition.

Those of skill in the art understand that the pudendal nerve is actually a pair of nerves with one pudendal nerve 104 on the right side of the body and one pudendal nerve 104 on the left side of the body. To avoid undue clutter, FIGS. 1-3 each show a single pudendal nerve 104 although the representation does include some of the branches within the pudendal nerve 104.

Those of skill in the art will recognize that there is the ability to stimulate the pudendal nerve 104 through the skin but this requires much greater electrical charge to initiate action potentials. Using higher level of electrical charge is not desirable for a variety of reasons including decrease of battery life. Thus, in most instances, the electrode should be placed as close to the pudendal nerve 104 as possible without risking damage of the pudendal nerve 104 during placement of the electrode.

Those of skill in the art will also recognize that there is the ability to stimulate the pudendal nerve through the skin using a magnetic coil or by surgically implanting a microcoil magnetic stimulator in close proximity to the pudendal nerve.

High Frequency Stimulation (HFS).

FIG. 3 diagrams the use of High Frequency Stimulation (HFS) 198 to produce a block 190 (represented figuratively by a large X) of physiologically-generated action potentials in axons from sphincter efferent motor neurons 120 in the sacral spinal cord 140 that mediate sphincter dyssynergia. Put another way, the HFS 198 blocks counterproductive nerve signals to the external urethral sphincter 134 that would prevent the external urethral sphincter 134 from complete relaxation. A lack of complete relaxation could cause the external urethral sphincter 134 to impede voiding urine driven by the contracting bladder 136.

Likewise, the HFS 198 blocks counterproductive nerve signals to the external anal sphincter 124 that would prevent the external anal sphincter 124 from complete relaxation. Again, a lack of complete relaxation could cause the external anal sphincter 124 to impede voiding feces driven by the contracting colon 126.

Thus, HFS helps the external anal sphincter 124 in the anal canal 128 and the external urethral sphincter 134 in the urethra 138 to open and stay open for voiding of feces and urine.

The electrode devices described herein use electrical pulses to allow an individual or patient to control the timing of micturition and/or defecation by manipulating pudendal nerve activity to switch from a storage mode to a voiding mode or from a voiding mode to a storage mode. The devices of this invention further improve the state of continence of the individual or patient when storing urine or feces. The combination of an improved state of continence with an "on-demand" voiding capability provides the patient, or those individuals responsible for their care, with control of these critical bodily functions without the use of intrusive procedures that are stigmatizing and can introduce the potential for infection or the use of drugs that can have side effects.

The pudendal nerve 104 carries somatic efferent innervation from sacral sphincter motor neurons 120, located in Onuf's nucleus, to the external urethral sphincter 134 and external anal striated sphincter 124, to bulbospongiosus and ischiocavernosus muscles, and associated striated muscles of the pelvic floor (Thor et al., 1989 J Comp Neurol. 1989 Oct. 8; 288(2):263-79, Yoo et al., 2008 Brain Res. December 30 1246:80-7; Barber et al., Am J Obstet Gynecol. 2002 July; 187(1):64-71; Thor and de Groat, 2010 Am J Physiol Regul Integr Comp Physiol. August 299(2):R416-38). The pudendal nerve 104 is required and sufficient for the striated sphincters 124 and 134 to contract; thus by continuously stimulating the pudendal nerve 104 during urine and feces storage, one can prevent incontinence. Manipulation of the frequency of the delivered pulse by the individual or patient during storage can further inhibit bladder contractions during storage of urine, contributing to an improved state of continence, with the ability to delay voiding until it is desirable to execute the voiding process.

In contrast, by temporarily blocking the pudendal nerve 104, the devices of this invention can block sphincter dyssynergia and allow voiding of the colon or bladder to proceed unimpeded when desired.

LFS.

Electrical stimulation of the pudendal nerve at low frequencies (1-16 Hz) inhibits involuntary, neurogenic, bladder contractions that can provoke urine leakage and incontinence (Peters, 2010 Neurourol Urodyn. September 29(7): 1267-71; Martens et al., 2011 J Urol. September 186(3): 798-804; Peters K M et al., 2005, Neurourol Urodyn. 24(7):643-7). This inhibition of the bladder 136 is mediated by stimulation of afferent fibers in the pudendal nerve 104. Primary afferent fibers from the perineum, external genitalia, urethra, and rectum traverse the pudendal nerve 104 and terminate in the superficial layers of the sacral dorsal horn and overlap with visceral sensory innervation afferent fibers of the bladder 130, colon 126, and genitalia (Thor et al., 1989) that subsequently inhibit bladder preganglionic neurons through spinal cord mechanisms. Inhibition of the bladder 130 by stimulation of genital afferent fibers (Martens et al., 2011) is thought to prevent bladder contractions from occurring during sex.

When the frequency of pudendal nerve 104 afferent stimulation increases to 20-33 Hz, the stimulation reportedly produces a bladder contraction through an excitatory sacral reflex. Between 10 and 20 Hz mixed effects might be obtained based on individual variability. A careful reader will note that the range of frequencies useful for closing the external urethral sphincter 134 extend beyond the low end of the range of frequencies that would excite the bladder/GI efferent neuron 130 to produce bladder contractions. Thus, a bladder 136 may be stimulated for contractions while the external urethral sphincter 134 remains constricted. While the constricted external urethral sphincter 134 will overcome the pressure to void from the constricted bladder 136, this may cause the patient to sense urgency with respect to emptying the bladder 136. Thus, one practiced in the art would make an empirical decision whether the benefit of increased frequency to produce more robust contraction of the sphincter provides sufficient benefit to counteract the loss of bladder inhibition.

Described herein are methods and devices that prevent incontinence and allow voiding with a simple "flipping of a switch" on the implanted pulse generator from the high frequency stimulation (HFS) (e.g. 5 kHz-20 kHz) pudendal nerve block (Voiding Mode) to low frequency stimulation (LFS) (e.g. 1-50 Hz) stimulation of efferent and afferent fibers in the pudendal nerve (Storage Mode), thereby obtaining both highly efficient voiding and prevention of incontinence between voids, respectively.

In an embodiment, the methods and devices described herein provide activation of both afferent and efferent fibers to inhibit the bladder 136 and contract the external urethral sphincter 134, respectively, to promote urinary continence that is superior to current devices. In an embodiment, methods and devices described herein contract the external anal sphincter 124 and optionally relax the sigmoid colon 126 to promote fecal continence.

In a further embodiment, these methods and devices are combined with drug-induced voiding, to further improve voiding efficiency. With this combination treatment, intermittent bladder catheterization, which is currently required multiple times per day for the lifetime of many individuals with spinal injury, can be eliminated or at least greatly reduced. This combination treatment also eliminates or greatly reduces the need for digital extraction of feces and/or use of enemas and suppositories.

Described within this disclosure document are methods to prevent incontinence using low frequency stimulation (LFS) of pudendal nerve efferent fibers to safely, tolerably, conveniently, and sufficiently contract the external urethral sphincter 134 and external anal sphincter 124 for the life of the patient with periodic relaxations to allow voiding.

The primary characteristic of the electrical signals in the methods and devices of this invention is pulse frequency, which at LFS parameters provides tonic contraction of the sphincters that elevates and maintains external urethral sphincter 134 and external anal sphincter 124 resistance to the point that physiologically relevant pressures (e.g. 10-40 cm H2O) generated by the bladder 136 or colon 126 are unable to expel urine or feces for the duration of time between voiding.

In other embodiments, the LFS parameters increase the force of contractions of the external urethral sphincter 134 and external anal sphincter 124 periodically to increase resistance to the point that physiologically relevant pressures (e.g. >100 cm H2O) generated by episodic abdominal muscle contractions, associated with voluntary physical exertion or during a cough or sneeze, are unable to expel urine or feces for brief periods of time (e.g. 1-10 min). For the LFS of the pudendal nerve, these signals range from about 0.1 to 50 Hz, or about 0.5 to 50 Hz, or about 1 to 50 Hz, or about 2 to 50 Hz, or about 5 to 50 Hz, or about 10 to 50 Hz, or about 0.1 to 20 Hz, or about 0.5 to 20 Hz, or about 1 to 20 Hz, or about 2 to 20 Hz, or about 5 to 20 Hz, or 0.1 to 10 Hz, or about 0.5 to 10 Hz, or about 1 to 10 Hz, or about 2 to 10 Hz, or about 5 to 10 Hz. In other embodiments, the LFS can be delivered as a brief (e.g. 10-100 ms) train of high frequency pulses (e.g. 20-100 Hz) delivered at the LFS ranges (e.g. 0.1-50 Hz).

FIG. 4.

Figure 4:
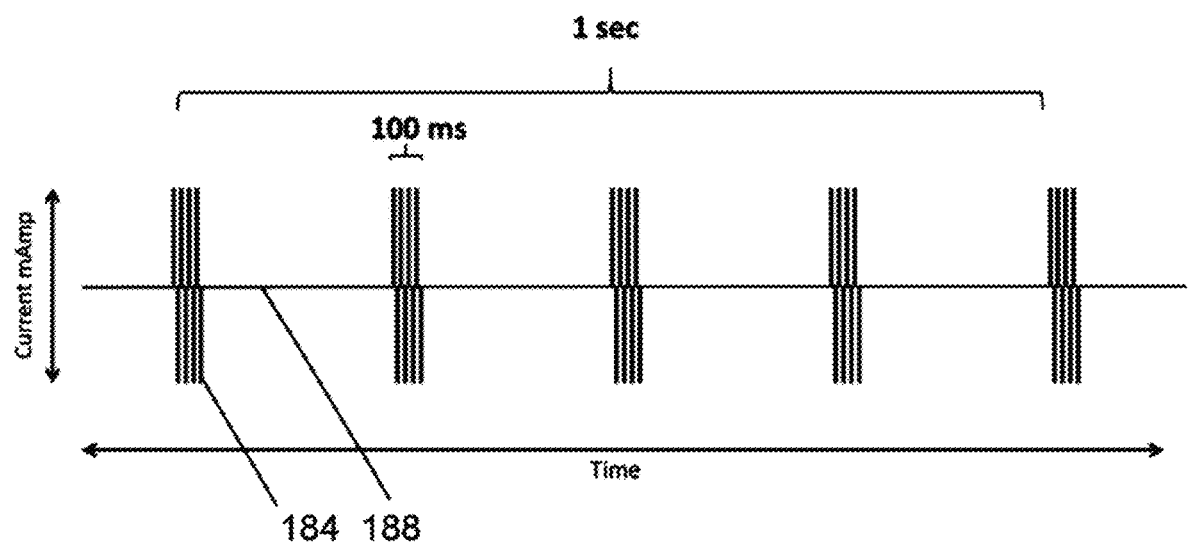
FIG. 4 shows a representation of an example of a pattern of LFS stimulation pulses.

FIG. 4 shows a representation of an example of LFS stimulation 194 applied as a train of pulses within each stimulation. In FIG. 4, a series of short (100 μsec) trains of 40 Hz pulses 184 applied for 100 ms are separated by gaps of time 188 (150 ms) without stimulation resulting in a 4 Hz train stimulation rate. As there are four stimulation trains of pulses 184 in one second, the frequency of the LFS is said to be 4 Hz. Note that within the train of pulses 184 of stimulation there are 40 Hz biphasic pulses for a train duration period of 100 ms which results in 4 trains of pulses 184 of 100 μsec each. Thus, the 100 ms periods of stimulation would have 400 μsec of stimulation (4 cycles*100 μsec) within a 100,000 μsec period (100 ms). One of skill in the art will appreciate that the representation in FIG. 4 has expanded the stimulation pulses within each train to allow for visualization. FIG. 4 is provided to make clear the role of trains of stimuli of the various frequencies noted with respect to LFS 194.

While FIG. 4 is useful to show a somewhat complicated LFS stimulation 194, the LFS stimulation 194 may be some other sequence of stimulation applied within the ranges set forth above (less than 50 Hz) and need not have higher frequency activity within pulse trains 184. The individual pulses may be simple square waves rather than trains of pulses 184.

A second characteristic of LFS is the pulse duration, which should be as short as possible to maintain the battery and prevent side effects and nerve damage but sufficiently long to depolarize the pudendal nerve axons. In embodiments, the pulse duration can range from 10 μsec to 500 msec or from 10 μsec to 1 msec or from 10 μsec to 0.5 msec.

A third characteristic of LFS is pulse amplitude which should be as low as possible to maintain the battery and prevent side effects and nerve damage but sufficiently large to depolarize the pudendal nerve axons. In some embodiments, the pulse amplitude can range from 0.001 to 50 mAmp or 0.01 to 20 mAmp which can be achieved using electrical potentials of 0.05-20 V or 0.1-10 V or 0.5-10 V.

Other characteristics of the electrical pulse (e.g., without limitation, polarity, number of phases per waveform (monophasic, biphasic, triphasic, etc.), and wave shape) can be varied as long as the pulse frequency, duration, and current are maintained within the stated ranges. It is recognized that charge balanced pulses theoretically produce less neural damage than unbalanced pulses, which provides an incentive to use biphasic or other waveforms to allow for charge balance rather than using monophasic waveforms. Stated ranges for LFS are intended to include all values and ranges within the stated ranges.

In an embodiment, the selected values for the above-described LFS can be in a range that also stimulates pudendal afferent fibers 110 (FIG. 2) to cause contractions of the bladder 136, so long as the external sphincters 124 and 134 resistance does not drop below levels that are required to resist flow created by physiologically relevant bladder pressure and colon pressure.

The combination of frequency, duration, and current within the above ranges that provides the greatest increase in sphincter resistance with the minimal amount of total electrical charge delivery to the nerve is termed the "pulse parameters" or "pulse characteristics" for LFS, i.e. the "Storage Mode", to be delivered by the pulse generator. The pulse parameters for an individual can be adjusted within these ranges by the individual or the attending caregiver to optimize them for inter-individual variability in electrode placement and physiological variability. This optimization ensures that minimal electrical charge is delivered to prevent nerve damage or other side effects while maintaining sphincter resistance at a clinically useful level. A secondary benefit of providing minimal electrical charge is to reduce charge drain from the battery.

Described herein are methods that provide effective and comprehensive control of bladder and colon function (i.e. control of both storage and voiding of urine and feces) by a single, implanted, and controllable pulse generator, interfaced with a single electrode for each pudendal nerve, wherein the patient or a caregiver attending the patient (a) prevents incontinence using low frequency stimulation (LFS) of pudendal nerve afferent and efferent fibers and (b) allows voiding of the bladder or colon using high frequency stimulation (HFS).

HFS Attributes.

The HFS is applied using a sinusoidal or quasi-sinusoidal waveforms or charge-balanced square pulses of about 1 kHz to 50 kHz, or about 1 kHz to 40 kHz, or about 1 kHz to 30 kHz, or about 1 kHz to 20 kHz, or about 1 kHz to 10 kHz, or about 1 kHz to 5 kHz, or about 5 kHz to 50 kHz, or about 5 kHz to 40 kHz, or about 5 kHz to 30 kHz, or about 5 kHz to 20 kHz, or about 5 kHz to 10 kHz or about 10 kHz to 50 kHz, or about 10 kHz to 40 kHz about 10 kHz to 30 kHz, or about 10 kHz to 20 kHz, or about 15 kHz to 50 kHz, or about 15 kHz to 30 kHz or about 15 kHz to 20 kHz. Stated ranges for HFS are intended to include all values and ranges within the stated ranges.

A second characteristic of HFS is the pulse duration of square wave pulses, which must be set at a duration that provides a continuous duty cycle (i.e. current is continuously applied as alternating positive or negative). One practiced in the art understands that to achieve a specific frequency of stimulation with a constant duty cycle requires a specific pulse width. For example, constant duty cycle stimulation at 1 kHz would require a pulse width of 1 msec; constant duty cycle stimulation at 10 kHz would require a pulse width of 100 μsec; constant duty cycle stimulation at 20 kHz would require a pulse width of 50 μsec; constant duty cycle stimulation at 50 kHz would require a pulse width of 20 μsec; etc. HFS should have a continuous duty cycle since even a brief period without a pulse (e.g. 50 μsec) can allow the nerve to recover its ability to conduct an action potential.

The pulses should be charge balanced to prevent nerve damage. The pulses need to be sufficient to depolarize the pudendal efferent axons and afferent neurons' axons. The biphasic charge balanced pulses could be square pulses or other shapes known in the art. The positive and negative biphasic charge balanced pulses do not need to be mirror images but need to have approximately the same total charge to limit side effects. One of skill in the art recognizes that sinusoidal waves also have a pulse duration that is dependent on the frequency of stimulation and are inherently charge balanced.

A third characteristic of HFS is pulse current amplitude which should be as low as possible to conserve battery life, limit side effects, and reduce nerve damage but sufficient to depolarize the pudendal efferent and afferent nerve axons associated with the sacral sphincter motor neurons 120. In embodiments, the pulse amplitude can range from 0.1 mAmp to 50 mAmp or 0.5 mAmp or 20 mAmp which can be achieved using electrical potentials of 0.05-20 V or 0.1-10 V or 0.5-10 V. According to Bhadra et al., 2006, higher frequencies of nerve block require higher voltages and current to affect a complete block, thus one would determine the minimum frequency that achieves complete block to reduce total electrical charge used.

The devices and methods described herein comprise a stimulating device having a pulse generator that can be turned on and off and switched between storage mode (LFS) and voiding mode (HFS) by the end users. In some embodiments, the frequency of the LFS pulses can be changed by the end user to increase sphincter contractions for periods of time according to their anticipation of an activity that can potentially precipitate leakage of fluid, and subsequent reduction of frequency to conserve battery life and prevent sphincter fatigue.

In some embodiments, the stimulating device is programmable, and the patient sets automatic switching from storage mode to voiding mode after a specified time limit in storage mode to allow release of urine or feces to prevent excessive stretch of the bladder or colon, which might cause damage, in instances when the end user is, for example, incapacitated. The time for storage mode is set at about 3 hours, about 4 hours, about 5 hours, about 6 hours, about 7 hours, or about 8 hours. In some embodiments, alerts are programmed, optionally through wireless communication, to be sent to the patient, caregivers, physician, or emergency personnel after specified time limits in storage mode in order to allow the device to be switched to void mode. In some embodiments, alerts can be sent to mobile phone devices, or to audio or visual alarms in the home.

In some embodiments, the pulse generator can be interfaced with a pressure sensing device implanted in the bladder, rectum, and/or abdomen in order to increase the stimulation frequency to achieve maximal sphincter contraction for brief periods (1-10 min) to counteract brief episodic increases in pressure that might temporarily exceed the typical physiological pressure (e.g. up to 200 mm Hg). While frequency is known as the primary driver of stimulation, increasing pulse amplitude or increasing pulse width may be used as secondary measures to increase stimulation. This would prevent incontinence that might occur when the patient is being moved from bed to wheelchair or preforming a Valsalva maneuver as occurs during sneezing or exercise.

In some embodiments, the pulse generator can be controlled by the end user to turn the stimulator off and on or to increase the stimulation parameters to achieve maximal sphincter contraction for brief periods (1-10 min) to counteract brief episodic or phasic increases in pressure (e.g. up to 200 mm Hg) that might temporarily exceed the tonic pressure in the bladder or rectum, in anticipation of physical exertion, such as transferring from wheelchair to bed, or in anticipation of a cough or sneeze.

EXAMPLES

Example 1.—Studies in Anesthetized Animals

FIG. 7 through FIG. 16 provide the results from a series of studies. These studies provide the parameters for reliable, physiologically significant contraction of the external urethral and external anal sphincter for therapeutic purposes. Pudendal nerve stimulation pulse frequency, duration, or current are systematically varied while the other two are held constant, while monitoring urethral and anal pressure to construct stimulus response curves (i.e. frequency-, duration-, and current-response curves). Effects of pudendal nerve stimulation on clinically relevant urodynamic variables (e.g. urethral pressure, bladder leak point or voiding pressure, bladder capacity, and voiding efficiency (chronic spinal)) can also be recorded. Similarly, effects of pudendal stimulation on clinically relevant colorectal manometric variables (e.g. anorectal pressure, anal opening pressure) can be recorded.

A. Experimental Design and Methods.

Anaesthetized animals are prepared for transvesical cystometry by inserting a catheter into the dome of the bladder to allow filling and recording of bladder pressure (BP). A catheter is also inserted into the urethra to record pressure with the tip positioned at the mid-urethral level (i.e. midpoint of striated muscle fiber distribution) while very slowly infusing saline to prevent occlusion of pressure recording by the wall of the urethra. Alternatively, a catheter with a microtransducer embedded in the tip can be inserted into the urethra. Animals are prepared for recording anal canal pressure by inserting a fluid-filled balloon catheter positioned in the anus at the midpoint of the striated anal sphincter or using a commercially available microtransducer, rectal manometry catheter (Mediwatch USA). The colorectal balloon catheter is gradually filled with saline until a baseline pressure of 8-15 mm Hg is attained.

Electrodes are placed on the pudendal nerves bilaterally at the ischial spine for stimulation and are attached to a pulse generator. Recording electrodes can be inserted into the urethral and anal rhabdosphincter to record EMG. In acute spinal animals, a laminectomy can be then performed to visualize the T10 spinal cord, and the spinal cord can be transected. This preparation is useful for eliminating secondary spinal reflex effects from modulating the direct effects of pudendal stimulation on the sphincter but eliminates distension-induced rhythmic bladder contractions which are required in order to assess PUD-mediated inhibition of the bladder activity (described below in Section C).

B. Optimization of LFS "Storage Mode" Pulse Parameters to Contract Sphincters.

The ranges of stimulation parameters to be reasonable for evoking action potentials on the pudendal nerve for chosen test animals are known from past experience and literature (Danuser and Thor, 1996 Br J Pharmacol. May 118(1):150-4; Tai et al., 2004 J Urol. November 172(5 Pt 1):2069-72; Tai et al. 2007 Neurourol Urodyn. 26(4):570; Thor and de Groat, 2010 Am J Physiol Regul Integr Comp Physiol. August 299(2):R416-38). Initially, all pudendal stimulation parameters were evaluated across a one- or two minute period of continuous stimulation. At a constant frequency of 0.5 Hz and pulse duration of 100 µsec, the amplitude of current (I) of the electrical pulses delivered by the stimulator was increased until a urethral and anal sphincter contraction occurs (recorded as a brief increase in urethral and anal pressure, see spikes in FIG. 7). The minimal amount of current required to stimulate the pudendal nerve in order to see a contraction of the sphincter was termed the threshold (I-T). Because the physical-spatial relationship between the electrode and the pudendal nerve is likely to vary during surgical placement of the electrode on or near the nerve, the I-T must be determined empirically. For this reason, it is expected that the I-T may differ between the right and left nerve in an individual and between individuals.

FIG. 7.

Figure 7:
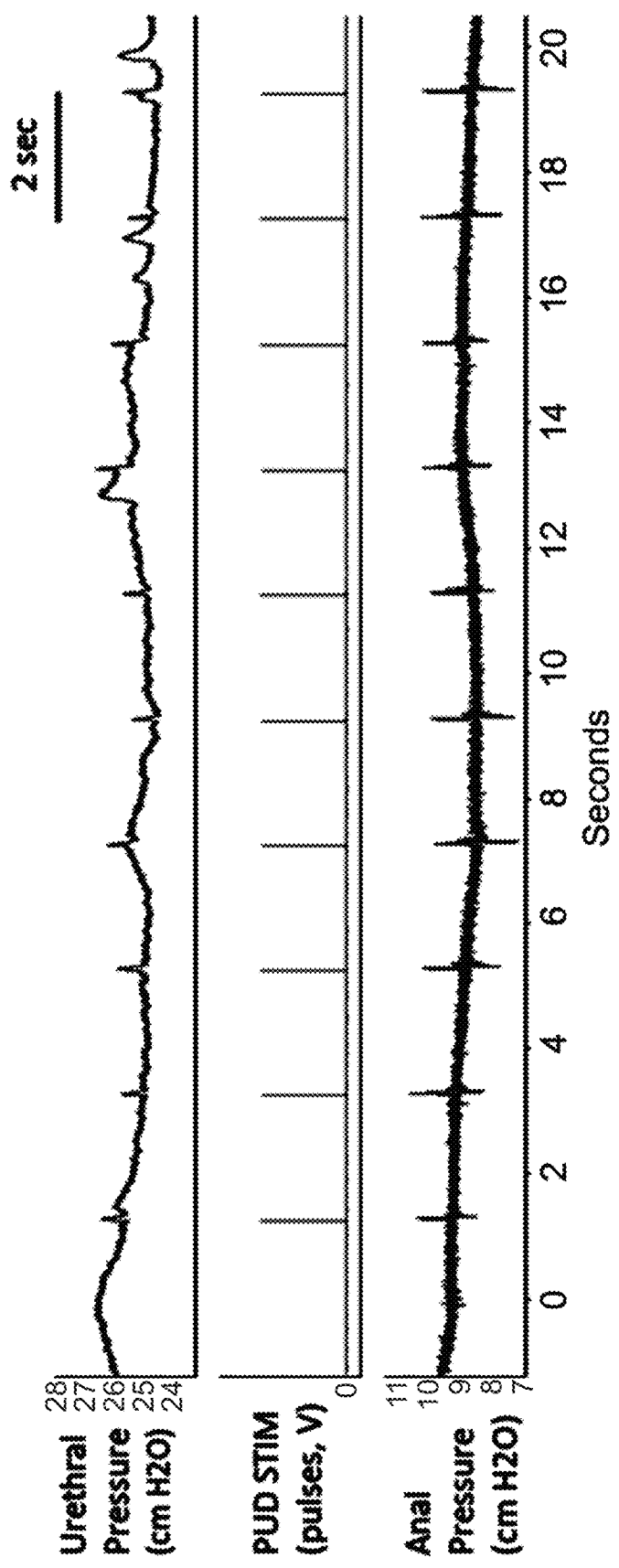
FIG. 7 is a physiograph tracing showing activation of the external urethral and external anal sphincters at the threshold current (I-T) of pudendal nerve stimulation.

FIG. 7 is a physiograph tracing of external urethral pressure (top trace), pudendal stimulation pulses (PUD STIM—0.5 Hz, 100 µsec duration; middle trace), and external anal sphincter pressure (bottom trace) demonstrating the threshold current (I-T) of 50 µA, which is virtually the same for activation of both sphincters. The horizontal axis is time, with a calibration bar=2 sec. Earlier testing, not shown here, determined that a current of 45 µA did not produce a contraction.

One of skill in the art familiar with such studies will know that the pressures recorded for the sphincters are measured by using catheters containing microtransducers in the tip of the catheter or by fluid-filled balloon catheters connected to strain gauge transducers. The precise placement of the microtransducer or fluid-filled balloons within the length of the urethra and anal canal, as well as the ability of a fluid-filled balloon to expand, can impact the pressure measured by these methods and thus do not provide absolute pressures but do provide relative pressures that can be seen to increase or decrease depending on the strength of the sphincter contraction. As the pressure readings are used to determine the relationship between pulse characteristics (i.e. current, pulse width, and frequency) and responses of the relevant sphincter, relative pressures are appropriate for this task.

The current amplitude that is required for a sphincter contraction (FIG. 7) defines the threshold current (I-T). Current is increased in increments (e.g. I-T, 2×I-T, 4×I-T, 6×I-T, 8×I-T . . . ) until further increases in current produce no further increases in sphincter pressure. This second current level is recorded as maximal response (I-max).

FIG. 8.

Figure 8:
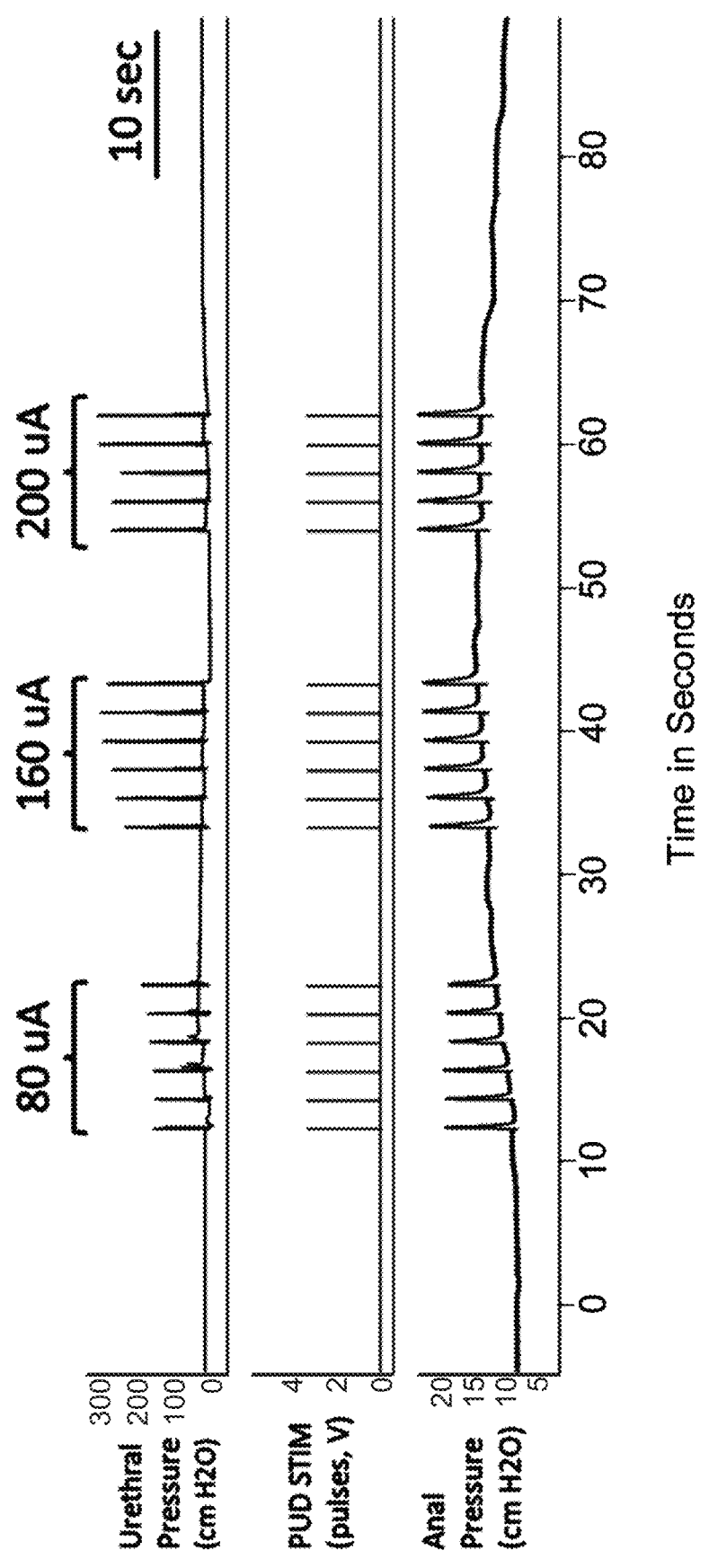
FIG. 8 is a physiograph tracing showing activation of the external urethral and external anal sphincters at the higher currents of pudendal nerve stimulation (i.e. current-response relationships).

FIG. 8 provides an example of the data seen by a person conducting this sequence of tests. More specifically, FIG. 8 shows physiograph tracings demonstrating current-response relationships of pudendal nerve stimulation and pressure increases in the external urethral sphincter (top trace) and external anal sphincter (bottom trace). Note that both the urethral and anal sphincter pressures are maximal at 160 µA, which is 3.2×I-T (50 µA) in this animal. Increasing current to 200 µA produces no further increase in pressure responses.

While stimulating at 50% of the I-max, pulse duration (µsec), also referred to as pulse width, was varied to determine threshold pulse width (PW-T) to evoke sphincter contraction. Pulse width was increased incrementally (T, 2T, 4T, 6T, 8T . . . ) to determine maximal response (PW-max).

FIG. 9.

Figure 9:
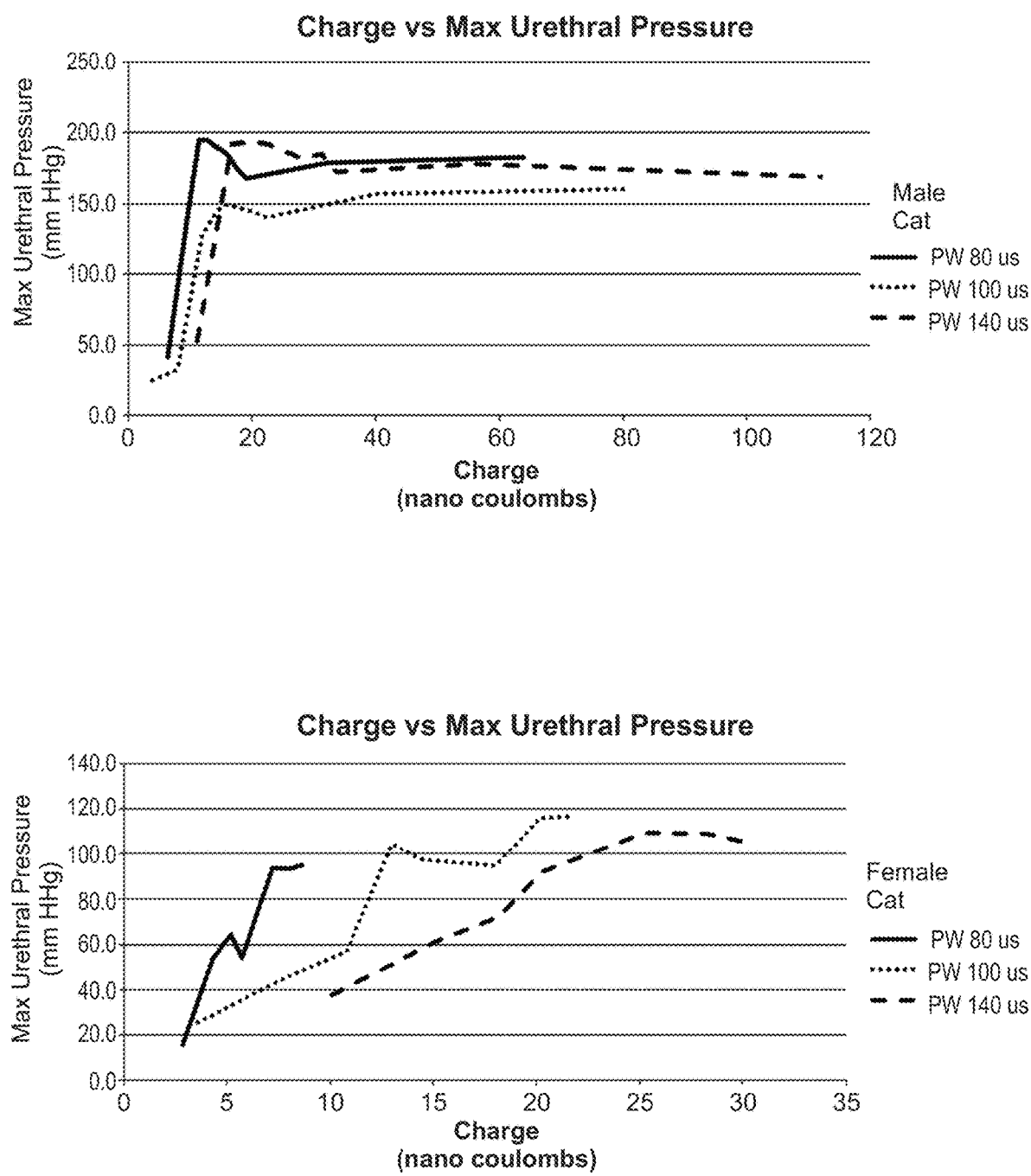
FIG. 9 shows graphs comparing the relationship between the amounts of charge required to produce urethral sphincter contractions at various durations of pulses applied to the pudendal nerve (i.e. pulse width-response relationships).

FIG. 9 illustrates one set of data. Data displayed in FIG. 9 shows that a pulse width (PW) of 80 µsec in male cats, and 40 µsec in female cats, produces greater maximal urethral pressure per unit charge than longer PWs when stimulating the pudendal nerve (1.5 I-T, 0.5 Hz). I-max, as noted above, was approximately 3×I-T (threshold current). Thus, 1.5 I-T is 50% of I-max. Maximum pressures in the male cat were nearly double those in the female cat. The female cat showed substantially less current was required at 40 µsec PW to achieve maximal pressure compared to the longer PWs, while differences were small for the male cat.

While stimulating at 50% I-max and 50% PW-max, the frequency of stimulation was increased logarithmically (0.5, 1, 2, 5, 10, 20, 50 Hz, etc.) to determine the threshold frequency (f-T) for increasing urethral and anal pressure above baseline for the stimulation period. Between tests of stimulation at a particular frequency, there was a baseline period of stimulation at 0.5 Hz. In addition, the frequencies are recorded at which:

1) summation of PUD-evoked contractions first occurs (i.e. where each subsequent pulse produces a larger pressure increase than the previous pulse; f-sum),
2) maximal maintained urethral and anal pressure is observed (f-max), and
3) fatigue of contraction first occurs (f-fatigue) during the one- or two minute period.

FIG. 10.

Figure 10:
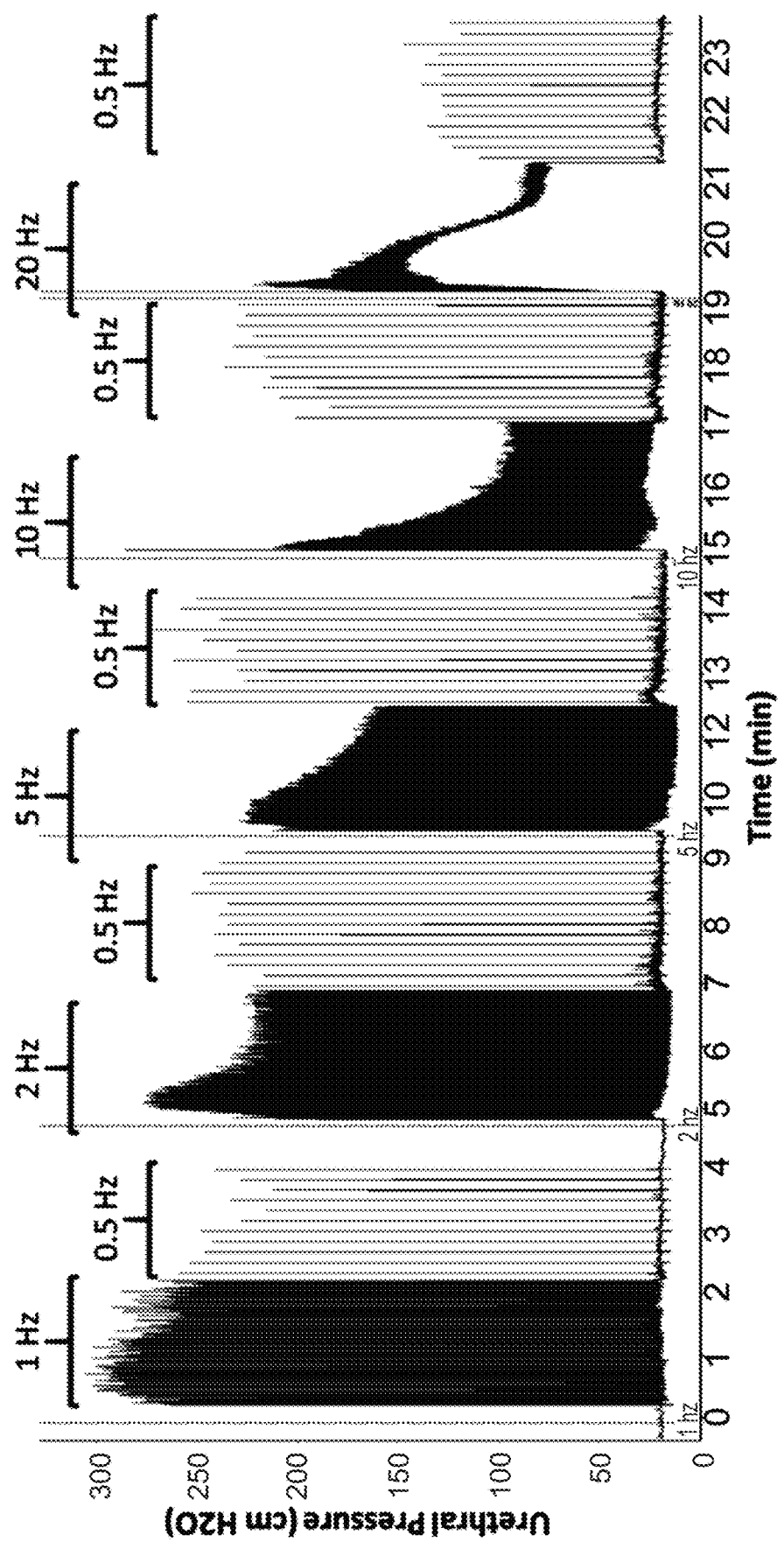
FIG. 10 is physiograph tracing showing activation of the external urethral sphincter at increasing frequencies of pudendal nerve stimulation (i.e. frequency-response relationship).

FIG. 10 shows frequency-response data from an experiment. Urethral pressure recordings showing the effects of various frequencies of pudendal nerve stimulation (1.5×I-T; 100 µsec PW). At frequencies >0.5 Hz, note that there was facilitation of the responses with the onset of stimulation (i.e. each stimulus, subsequent to the first, becomes progressively larger) until fatigue of the response occurs (i.e. each stimulus subsequent to the stimulus producing the largest response becomes progressively smaller) until a plateau in the response was reached (i.e. each stimulus produces a response similar to the one preceding and following it).

Note that, at frequencies >1 Hz, there was an elevation in baseline pressure with the onset of stimulation. This elevation in baseline pressure during stimulation was due to summation of a subsequent stimulus's response (i.e. elevation in urethral pressure) being superimposed on the preceding stimulus's response before pressure returns to baseline. Note that the elevation was small and transient at 2 and 5 Hz, due to fatigue overshadowing the summation, but summation is maintained at 10 and 20 Hz. The baseline pressure at 10 Hz was smaller than at 20 Hz (i.e. ~30 cm H2O and ~80 cm H2O). During the absence of summation, drop of urethral pressure to low levels between pulses could allow fluid to leak from the bladder between stimulus pulses when the bladder pressure is greater than the urethral baseline pressure. Thus, an elevation in baseline pressure is preferred.

Note that this same cuff electrode was used to block the PUD nerve in FIG. 16 (discussed below), demonstrating that the same electrode can be used to stimulate and block the pudendal nerve.

Subsequently, holding the frequency constant at f-max and the pulse duration at 50% max, the pulse current was reduced to I-T and the current-response curve was reconstructed. Similarly, holding the frequency constant at f-max and the current to the 50% max, the pulse width was reduced to PW-T and the pulse duration-response curve was reconstructed. This iterative process was repeated until a balance of the three parameters provided the desired increase in sphincter resistance with minimal amount of electrical charge, i.e. Storage Mode parameters. Subsequently, this balanced pulse characteristic (e.g. a 10 µA pulse of 50 µsec duration applied at a frequency of 20 Hz) was then applied to the pudendal nerves while recording urethral and anal pressure for a two-hour period to ensure that the stimulation parameters maintain stable elevation in urethral and anal sphincter pressures. If pressures were not maintained for the two-hour test period, the frequency of the stimulus was reduced until the elevation in urethral and anal sphincter pressures was maintained for the two-hour test period (see FIG. 13 and FIG. 14 for two-hour duration demonstration).

FIG. 11.

Figure 11:
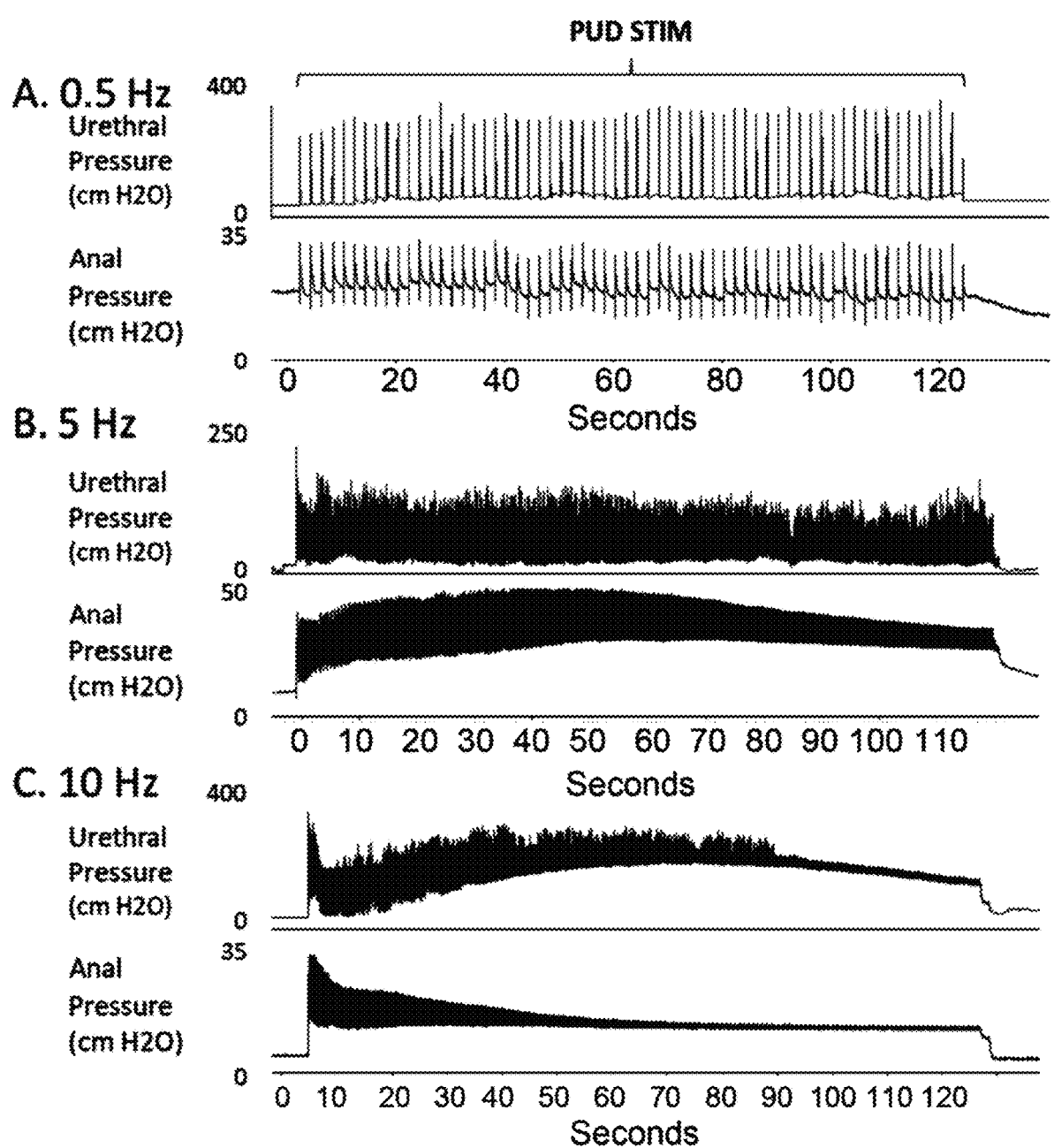
FIG. 11 shows physiograph tracings comparing frequency-response relationships of pudendal nerve stimulation on the external urethral and anal sphincters.

FIG. 11 shows data from the step examining the ability of various frequencies of stimulation to maintain baseline pressures for 10 minutes and the frequency-response relationship of pudendal nerve stimulation (PUD STIM) on anal and urethral sphincter pressures.

A. Low frequency stimulation at 0.5 Hz elevates both anal and urethral pressure briefly, but pressure dropped to the original baseline prior to the subsequent stimulus.

B. At 10 Hz, summation of both urethral and anal pressures (i.e. pressure response from preceding stimulus did not return to baseline before subsequent stimulus's response occurs) maintained a small elevation in urethral and large elevation in anal baseline pressures.

C. At 10 Hz, summation of urethral and anal sphincter contractions produced large elevations in baseline pressure of both.

Urethral Pressures.

One practiced in the art understands that elevating the urethral pressure above diastolic blood pressure will reduce blood flow to the urethral tissue and exceeding the systolic blood pressure will prevent blood from perfusing the urethra and produce ischemia. Thus, for clinical use, it is understood that maintaining urethral pressure above the average healthy human's systolic/diastolic pressure (e.g. typically 120/80 mm Hg=163/108 cm H2O) for more than a few minutes could damage the urethral and anal sphincters. Conversely, maintaining urethral and anal pressure safely below the minimum range of diastolic pressures that one would expect to encounter in the general population (i.e. 60 mm Hg=81 cm H2O) for prolonged durations (i.e. all day) should allow adequate perfusion of the urethra and anal canal. One practiced in the art also recognizes that bladder contractions during volitional urination in healthy individuals can produce brief (i.e. ~2-3 min) elevations in pressure to 40 cm H2O, and in individuals with bladder hypertrophy, contractions can produce pressures in excess of 80 cm H2O.

Need for Brief Periods of Elevated Contraction Pressure.

During brief periods of exertion that result in elevation of abdominal pressure (and subsequently pressure transferred to the bladder and rectum), such as in anticipation of a cough or sneeze or exercise or a subject's transfer from bed to wheelchair and back, it is practical to increase the urethral or anal contraction pressures to their maximal force for those brief periods of time. These values are useful as context for demonstrating that pudendal nerve stimulation can elevate urethral pressure for short periods of time (i.e. 2-10 min) to pressures in excess of 100 cm H2O such as seen in FIG. 10, FIG. 11, and FIG. 12 and can elevate leak pressure from the bladder in excess of 40 cm H2O for prolonged periods of time (e.g. 2 hours) as seen in FIG. 13.

FIG. 12.

Figure 12:
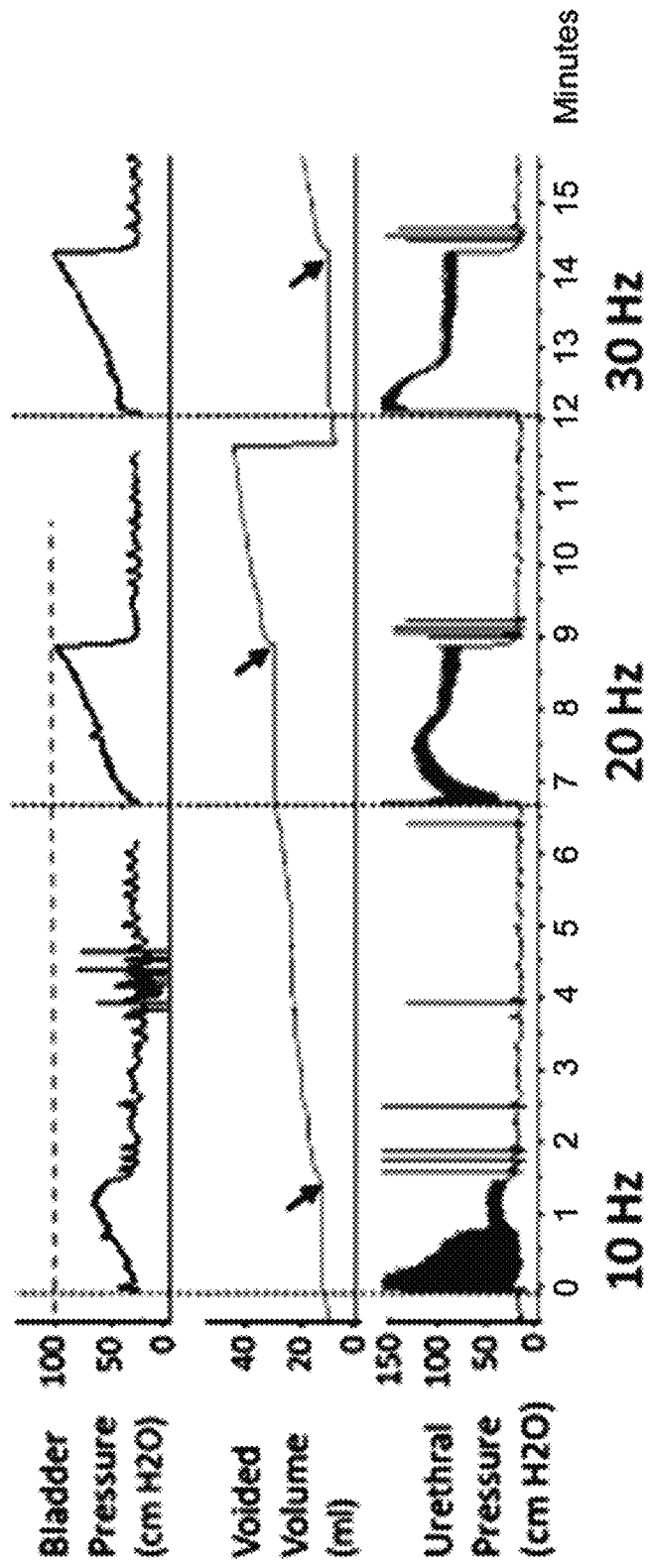
FIG. 12 shows physiograph tracings of bladder pressure, volume of fluid released, and urethral pressure before and during pudendal nerve stimulation, which prevented fluid release from the bladder.
Figure 13:
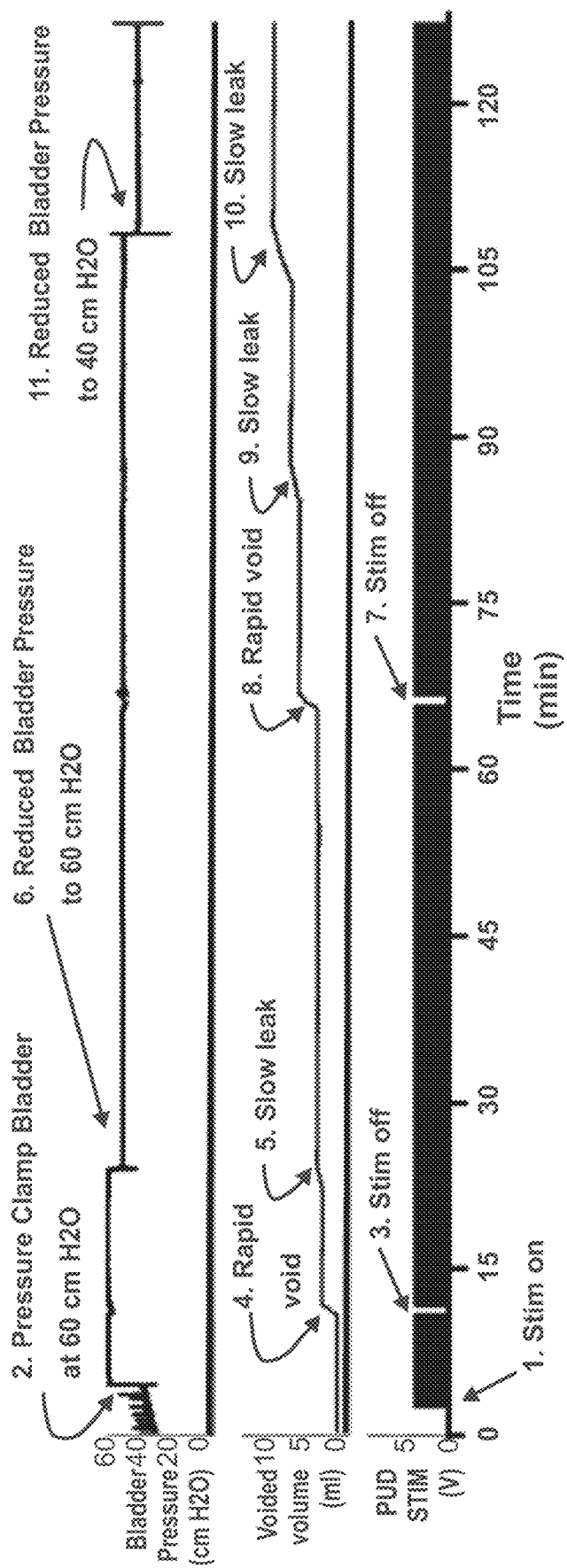
FIG. 13 shows physiograph tracings of bladder pressure, volume of fluid released, and pudendal nerve stimulation pulses before and during pudendal nerve stimulation, with brief interruptions of pudendal nerve stimulation, which demonstrates that pudendal nerve stimulation can prevent the release of fluid for over 2 hours under conditions of clinically significant elevated bladder pressures.

FIG. 12 shows test data indicating that PUD stimulation at 20 Hz or 30 Hz allowed the bladder to fill until a bladder pressure of 100 cm H2O was reached with no fluid leaking from the urethra (i.e. the slope of the voided volume tracing is zero) during pudendal nerve stimulation. At 100 cm H2O the stimulation was stopped to avoid overfilling the bladder. When the pudendal nerve stimulation was stopped, fluid was released from the urethra (i.e. the slope of the voided volume trace becomes positive with time). Stimulation at 10 Hz prevented fluid from escaping the urethra until the bladder pressure reached 60 cm H2O as a result of continued infusion of saline without release of fluid. With no pudendal nerve stimulation, the bladder released fluid at the same rate at which it was infused when the bladder pressure reached 30 cm H2O.

A method of demonstrating that LFS pudendal nerve stimulation can prevent the leakage of fluid from the bladder for specific periods of time is to "clamp" the bladder pressure for the specific period of time. To "pressure clamp the bladder", one end of the bladder catheter was attached to a fluid reservoir that was set at a known height above the level of the bladder, while the other end remains attached to a pressure transducer. Adjusting the height of the column to 60 cm above the bladder produced a pressure of 60 cm H2O in the bladder; adjusting the height of the column to 50 cm above the bladder produced a pressure of 50 cm H2O in the bladder; and adjusting the height of the column to 40 cm above the bladder produced a pressure of 40 cm H2O in the bladder; etc.

When the external urethral sphincter contraction was strong enough to prevent the flow of fluid from the bladder at a given pressure, no fluid escaped from the bladder, but if the sphincter contraction is not strong enough to resist the flow of fluid at a given pressure, fluid escaped from the urethra. To determine if, and the volume of, fluid that escapes from the urethra, fluid was collected in a vessel and the weight of the vessel and fluid was measured with a strain gauge transducer that was calibrated to convert weight to volume contained in the collecting vessel. The voided volume recorded in this manner shows a flat line on the physiograph tracing when no fluid was being released and shows an increase in slope that is proportional to the rate of fluid released when release occurs. (See arrows in FIG. 13 showing the change in slope of voided volume trace from a flat line to a sloped line when voided fluid is detected and recorded.)

FIG. 13.

FIG. 13. Demonstration that pudendal nerve stimulation can prevent leakage of fluid from the bladder during prolonged (i.e. over 2 hours) elevation of bladder pressure. Physiograph tracings show bladder pressure (top), cumulative void/leak volume (middle), and pudendal stimulus pulses (bottom). Taken together, these three tracings show the ability of pudendal stimulation to maintain the bladder leak point pressure (LPP) at >40 cm H2O for a two-hour period. The following is the list of experimenter actions, and the effect of each action, for each point indicated by the numbered arrows in the figure.

1. Start bilateral, electrical stimulation (20 Hz, 3×I-T—120 µA left, 150 µA right 100 µsec) of the PUD nerves (pudendal stimulation).

2. After 1 minute, bladder pressure was elevated and "clamped" at 60 cm H2O by placing a catheter into the bladder through the detrusor muscle and connecting it to a large reservoir of saline adjusted to a height of 60 cm. Pressure was maintained, and no leakage of fluid occurred, indicating that the LPP was >60 cm H2O.

3. After 10 min, pudendal stimulation was briefly turned off (2 minutes), and then back on, to demonstrate that fluid maintained at this pressure in the bladder would be rapidly voided through the urethra without pudendal stimulation and be recorded by the voided volume apparatus.

4. Rapid void of fluid was recorded during the 2-minute period when pudendal stimulation was off, and fluid leaking stops when pudendal stimulation is turned on again.

5. Twenty minutes after starting pudendal stimulation, a slow leak of fluid was recorded, indicating that the LPP at that time is <60 cm H2O.

6. The height of the reservoir is reduced to 50 cm, i.e. bladder pressure was reduced to 50 cm H2O, and leakage stops, indicating that the LPP is between 50-60 cm H2O.

7. Sixty-five min after starting pudendal stimulation, pudendal stimulation was briefly turned off (3 min) as in #3.

8. Rapid release of fluid was again observed, indicating that pudendal stimulation was responsible for maintaining LPP>50 cm H2O.

9. Seventy-five min after starting pudendal stimulation, a slow leak of fluid was recorded for 3 minutes, but before investigator can lower the column, the leak stopped.

10. More than 95 minutes after starting pudendal stimulation, a slow leak of fluid was recorded for a longer time (5 min), indicating that the LPP at that time was <50 cm H2O.

11. The height of the reservoir was reduced to 40 cm, i.e. bladder pressure was reduced to 40 cm H2O, and leakage stops, indicating that the LPP is now between 40-50 cm H2O. This is considered a clinically significant elevation in leak point pressure (LPP) and a pressure higher than 60 cm H2O throughout the day could possibly cause a reduction in blood flow to the urethra throughout the day and thus produce ischemia and tissue damage. No further leakage of fluid from the bladder was observed for the remainder of the 120 minutes of pudendal stimulation.

Rectal Pressures.

Resting rectal pressure ranges from 1.0-60 cm H2O, and during volitional defecation can range from 175 cm H2O to 250 cm H2O due to conscious "bearing down" (i.e. Valsalva maneuver) using abdominal muscles to increase pressure. This Valsalva pressure can also be passively transferred to the bladder. The Valsalva maneuver cannot maintain abdominal, bladder, and rectal pressures at this elevated level for more than a couple of minutes without a pause required for inhalation, which is required after a minute or two of holding one's breath during the Valsalva maneuver. Thus, maintaining pudendal stimulation-induced increases in urethral and anal pressure to prevent leakage of urine or stool at a level below diastolic pressure, but above the individual's resting urethral and anal pressure, should eliminate or reduce incontinence episodes throughout most of the day.

However, during brief periods of exertion that result in elevation of abdominal pressure (and subsequently pressure transferred to the bladder and rectum), such as in anticipation of a cough or sneeze or exercise or a transfer from bed to wheelchair and back, it is practical to increase the urethral or anal contraction pressures to their maximal force for those brief periods of time.

A method of demonstrating that LFS pudendal nerve stimulation can elevate anal sphincter pressure for prolonged periods of time is done simply by recording anal canal pressure for the specific period of time as described in section A.

FIG. 14.

Figure 14:
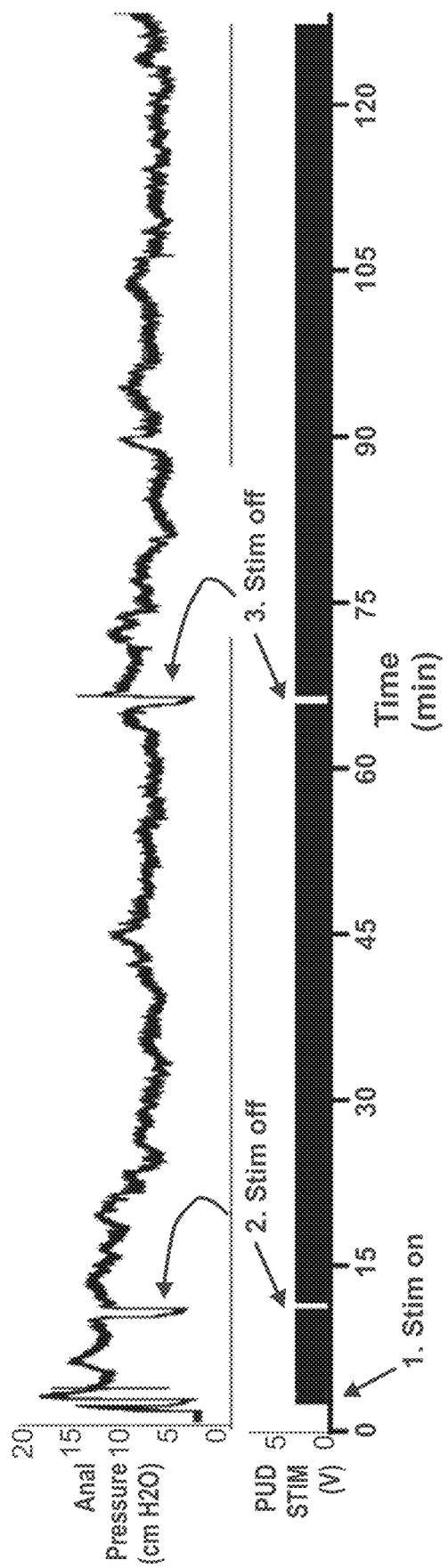
FIG. 14 shows physiograph tracings of anal pressure and pudendal nerve stimulation pulses before and during pudendal nerve stimulation, with brief interruptions of pudendal nerve stimulation, which demonstrates that pudendal nerve stimulation can elevate anal pressure for over 2 hours without fatigue of the external anal sphincter.

FIG. 14 demonstrates that LFS pudendal nerve stimulation can maintain an elevation in external anal sphincter pressure for more than 2 hours. Physiograph tracings of anal pressure were stably maintained above baseline for over 2 hours during the course of bilateral pudendal nerve stimulation (STIM; 20 Hz, 3× threshold current (120 μA left, 150 μA right) 0.1 msec. Pudendal nerve stimulation may be abbreviated as PUD stimulation. At arrow #1, PUD STIM was started. At arrow #2, PUD STIM was stopped for 2 min then re-started to demonstrate that PUD STIM was required to maintain the pressure elevation. At arrow #3, PUD STIM was stopped for 3 min then re-started. Notice the drops in rectal pressure when PUD STIM was interrupted.

C. Optimization of LFS "Storage Mode" Pulse Parameters to Also Inhibit the Bladder while Simultaneously Contracting the Sphincters.

The question of interest is whether the same PUD stimulation that activates PUD efferent fibers to cause contraction of the external urethral sphincter and thus elevate urethral pressure (sufficiently to prevent leakage of fluid from the bladder) has a second benefit. The second benefit is activating PUD afferent fibers that inhibit bladder activity through spinal mechanisms, thus delaying the onset of, and decreasing the magnitude of, non-voiding contractions (NVCs). Non-voiding contractions (NVCs) are thought to be responsible for episodes of urinary incontinence. The combination of these two synergistic benefits would be to increase the amount of fluid that the bladder can hold prior to leaking fluid.

To demonstrate inhibition of bladder activity, starting with an empty bladder, the bladder was infused at 2 ml/min while recording bladder pressure, voided volume, and urethral pressure until voiding was observed as an increase in voided volume. (The onset of voiding is indicated by arrows on the voided volume tracings in FIG. 15.) Similar to the above protocol to record the effects of pudendal stimulation on sphincter pressure, stimulus response curves (current-, duration- and frequency-response) were created to determine which set of balanced parameters produce inhibition of the bladder contractions.

FIG. 15.

Figure 15:
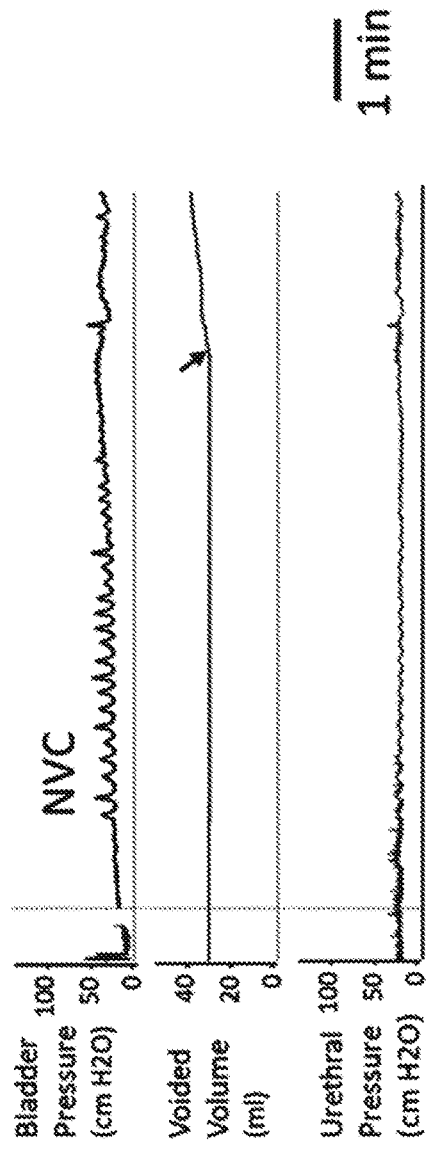
FIG. 15 shows physiograph tracings of bladder pressure, volume of fluid released, and urethral pressure during bladder infusion of fluid, with and without pudendal nerve stimulation, which demonstrates that pudendal nerve stimulation can inhibit bladder activity and increase the amount of fluid that can be held in the bladder before fluid leaks from the bladder.
Figure 15:
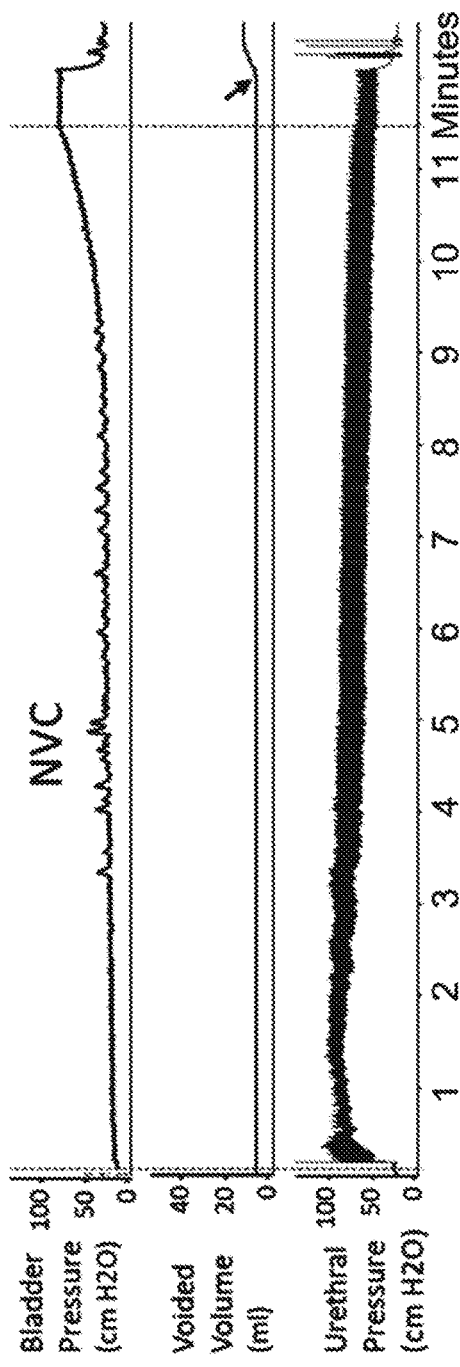

FIG. 15 shows data that demonstrates exactly this combination of benefits. FIG. 15 shows that the same stimulation parameters that activate PUD efferent fibers to cause contraction of the external urethral sphincter and thus elevate urethral pressure (sufficiently to prevent leakage of fluid from the bladder) also activate PUD afferent fibers that inhibit bladder activity through spinal mechanisms, thus delaying the onset of, and decreasing the magnitude of, non-voiding contractions (NVCs), which are thought to be responsible for episodes of urinary incontinence, and thus increasing the amount of fluid that the bladder can hold prior to leaking fluid.

In FIG. 15, there are three physiograph tracings per set of data. There is one set of data to show bladder response without PUD stimulation and another set of data showing bladder response with PUD stimulation. The three tracings are:

The top tracing showing bladder pressure.

The middle tracing showing the volume of fluid released ("voided volume").

The bottom tracing showing urethral pressure during cystometrograms (CMGs).

In each case, starting with an empty bladder, the bladder was infused at 2 ml/min while recording bladder pressure, voided volume, and urethral pressure until voiding was observed through an increase in voided volume. The onset of voiding is indicated by arrows on the voided volume tracings. After establishing control values, cystometry was repeated with pudendal stimulation at the Storage Mode parameters.

Observations on Data without PUD Stimulation.

Note frequent non-voiding contractions (NVC) starting soon after 1 minute of infusion (i.e. 2 ml bladder volume).

Voiding occurred after 5 minutes and 30 seconds (i.e. 11 ml bladder volume) at a bladder pressure of 40 cm H2O.

Observations on Data with PUD Stimulation.

PUD stimulation was applied (20 Hz, 0.1 ms, 3×I-T). NVC during PUD stimulation were not detected until 3 minutes (i.e. 6 ml; a 3-fold increase compared to without PUD stimulation) and leakage of fluid was not detected until 10 minutes 30 seconds (i.e. 21 ml bladder volume; a 1.9-fold increase in bladder capacity compared to without PUD stimulation) at a bladder pressure of 80 cm H2O (i.e. a 2-fold increase compared to without PUD stimulation). When PUD stimulation was stopped, the bladder rapidly (<15 sec) voided 7 ml (see indicator arrow), and bladder pressure dropped to baseline levels. Note that the time scale is consistent across the two sets of data.

The optimal bladder inhibition may be at 5 or 10 Hz which can be below the optimal sphincter contraction, which may be at 20 Hz; it may not be possible to optimize both. Because the sphincter resistance can be elevated to completely block flow at the highest ranges of safe physiological bladder pressures, the stimulus parameters for achieving optimized sphincter contraction hold precedent over optimized bladder inhibition as sphincter control is the primary tool for avoiding incontinence. In other words, the method of preventing incontinence would function without bladder inhibition, but it would be preferred to both suppress bladder activity and contract the sphincters to prevent sensations of urinary urgency. Thus, as demonstrated in FIG. 15, optimized stimulus parameters for sphincter contractions can provide sufficient elevations in urethral resistance to prevent incontinence and also provide some bladder inhibition.

D. Evaluation of a Single Electrode to Each Pudendal Nerve to Provide Both the Optimized LFS "Storage Mode" Pulse Parameters, as Well as the HFS "Voiding Mode" Parameters.

Urethral pressure was recorded as described in section A. In addition to the 2 electrodes placed on each of the pudendal nerves, a third electrode was placed on the S1 spinal root. Many pudendal nerve efferent fibers exit the spinal cord through the S1 root, along with fibers that contribute to hindlimb nerves (e.g. the sciatic nerve). The PUD fibers split from the S1 root a short distance (e.g. 1-3 cm) after the spinal root emerges from the S1 vertebral column. Thus, pudendal nerve efferent fibers that exit the spinal cord in the S1 root will first pass the S1 spinal root electrode and, after branching to join the pudendal nerve, will pass the pudendal nerve electrode as they continue to the external urethral and anal sphincters. Thus, electrical stimulation of the S1 root will produce an action potential in PUD efferent fibers (similarly to stimulation of the fibers with the electrode placed more distally on the PUD nerve itself). These action potentials then travel along the pudendal nerve, past the pudendal nerve electrodes, and produce a contraction of the external urethral and anal sphincter muscles, producing a urethral pressure spike. Because the S1 root-evoked action potentials must pass the pudendal nerve electrode prior to reaching the external urethral sphincter, blockade of the action potentials by the pudendal nerve electrode will prevent the S1 root-evoked action potentials from reaching the external urethral sphincter, and no pressure spike will be seen. Thus the S1 root stimulation provides a "monitor" to determine if application of high frequency (i.e. 25 kHz) electrical pulses applied to the PUD nerve (HFS) has blocked conduction of the action potentials from reaching the urethral sphincter muscle.

FIG. 16.

Figure 16:
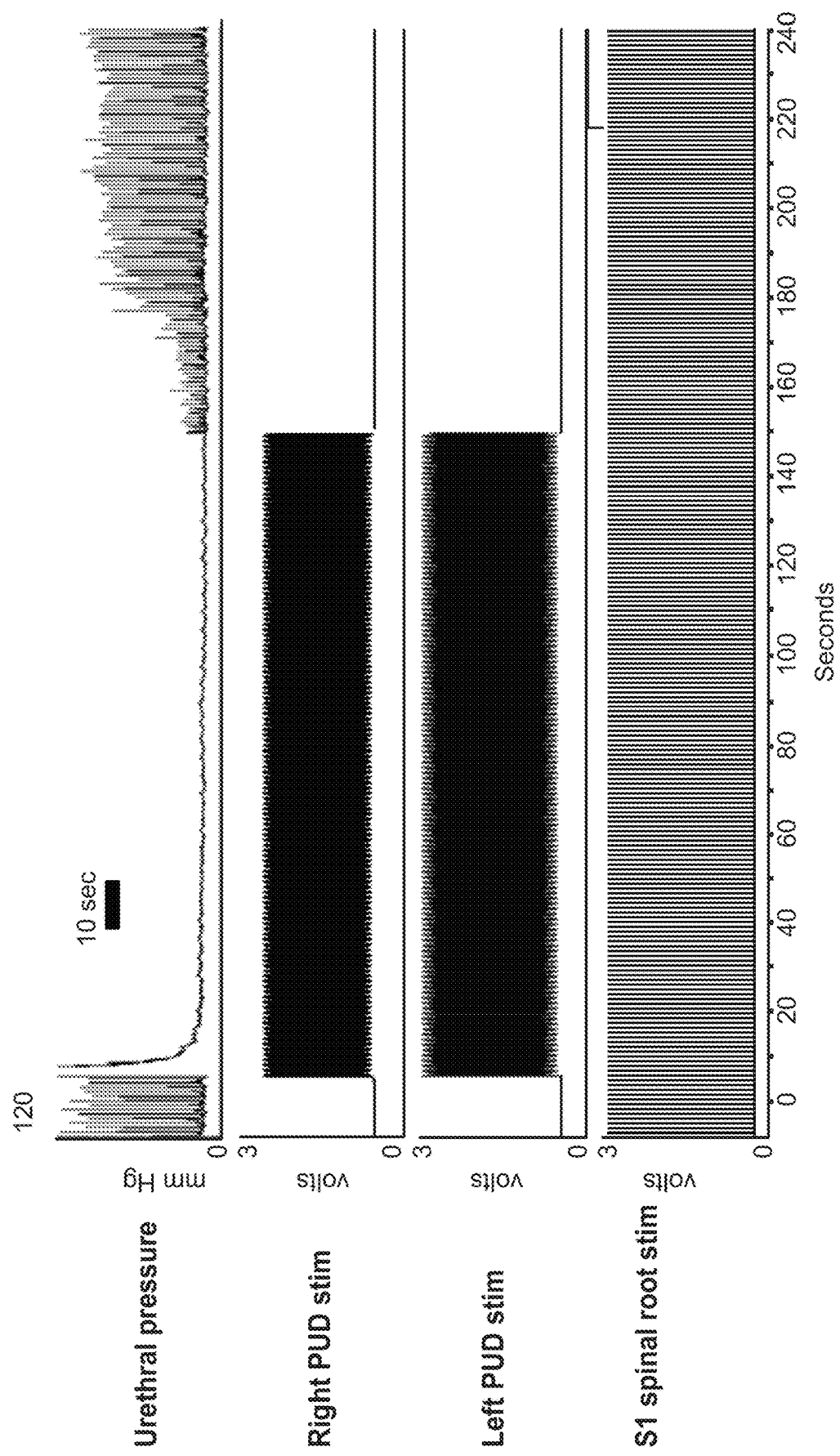
FIG. 16 shows physiograph tracings of urethral pressure and stimulation pulses applied to the left and right pudendal nerve and the right S1 spinal root, which shows that HFS of the pudendal nerves can prevent the activation of the external urethral sphincter by S1 spinal root stimulation using the same electrode that was used to stimulate the pudendal nerve at LFS to contract the sphincter.

FIG. 16 shows physiograph tracings of urethral pressure (top panel) and stimulus pulses applied to the right and left pudendal nerve (PUD, second and third traces, respectively) and to the right S1 sacral root (bottom panel).

This data demonstrates that the same electrodes used to stimulate PUD efferent and afferent fibers to contract the sphincter and inhibit the bladder, respectively, using low frequency stimulation (i.e. 10-20 Hz), can also be used to apply high frequency (25 kHz) bilateral pudendal stimulation to block pudendal nerve fibers from conducting action potentials and thus cause the external urethral sphincter to relax.

FIG. 16 has a set of four physiograph tracings. The four monitored items are:

Top tracing—urethral pressure.

Upper-middle tracing—stimulus pulses applied to the right pudendal nerve (PUD).

Lower-middle tracing—stimulus pulses applied to the left pudendal nerve (PUD).

Bottom tracing—stimulus pulses applied to the S1 sacral root.

E. Evaluation of Pudendal Stimulus "Voiding Mode" Parameters to Improve Drug-Induced Voiding.

The use of pudendal stimulus may be coupled with drug induced voiding. This combined approach can be evaluated. The process for this evaluation could be as follows. Cystometry is performed as described in section A without urethral occlusion in acute or spinal animals with compromised bladder function that prevents complete voiding (i.e. voiding efficiency <100%). Cystometry is first conducted without pudendal stimulation to establish bladder volume capacity and leak point pressure. Bladder and urethral and anal sphincter pressures are recorded. The bladder is then filled to 70% of capacity and a fluid-filled balloon is inserted into the rectum from the aboral colon with a baseline pressure of 10-20 mm Hg (Maggi et al., 1988 Gen Pharmacol. 19(4): 517-23, Naitou et al., 2016 Physiol. 2016 Aug. 1; 594(15): 4339-50 Epub 2016 Apr. 28). A short-acting agent that activates the bladder and colon to induce micturition and defecation (e.g. bladder and colon prokinetic agents such as an NK2 receptor agonist such as [$Lys^5$,$MeLeu^9$,$Nle^{10}$]-neurokinin $A_{(4\text{-}10)}$) is administered, and the volume of fluid expelled from the bladder and from the colorectal balloon, as well as the pressures in the bladder and colorectal balloon, are recorded.

After sufficient time to allow recovery from the first administration of bladder and colon prokinetic agent, the bladder and colorectal balloon are again inflated to a volume of 70% of bladder capacity and to a pressure of 10-20 mm Hg, respectively. One minute prior to administration of the prokinetic agent, the pudendal stimulation using "Voiding Mode" pulse parameters is applied. The prokinetic agent is administered and the volume of fluid expelled from the bladder and from the colorectal balloon, as well as the pressures in the bladder and colorectal balloon, is recorded.

Example 2—Long-Term Evaluation

Example 2 sets forth the process to look at the long-term evaluation of clinical benefits of a device to prevent incontinence and allow drug-induced voiding in animals with spinal cord injury.

A. Methods for Incontinence Control.

Under sterile techniques, anesthetized animals undergo T10 transection and implantation of Synapse System Pulse Generator connected to tripolar pudendal electrodes (electrodes similar to Synapse System in principle but modified for size of animal). During implantation, the threshold current (I-T) for inducing a visible twitch of the perineum is measured, and the current is increased to a multiple of the threshold based on the results above. Before each test day, the threshold for inducing a twitch in the animal is measured, and if it changes, the working current is adjusted to a multiple of the new threshold. After post-op recovery, the animals are housed in a metabolism cage, which has a lining of "plastic air bubble" packing material placed on the floor (to prevent pressure ulcers). Twice daily, animals' bladders will be emptied by Credé maneuver (morning and 8-10 hours later). Every day, except weekends and holidays, are "test days" simulating chronic, continuous use of the implantable, programmable, pulse generator in a clinical setting.

This animal model simulates the human condition in many aspects of spinal injury and is large enough to accept an implanted pulse generator. The behavioral studies use the clinically relevant measure of incontinence episode frequency and volume of urine and weight of feces with, versus without, low frequency pudendal stimulation and measures the clinically relevant end-point of voiding efficiency during "physiological" and "[Lys$^5$,MeLeu$^9$,Nle$^{10}$]-neurokinin A$_{(4-10)}$-induced" voiding with, versus without, high frequency pudendal block.

On test days (after checking pudendal stimulation threshold current for inducing a visible twitch of the perineum), low frequency pudendal stimulation is applied across the eight-hour test period, or (on a randomized, blinded basis) the animal has the pudendal stimulation turned off.

B. Measurements.

On test days, a layer of Whatman 4 filter paper (cut from a 3' wide roll provided by manufacturer) is placed on top of the plastic bubbles to completely cover the floor of the cage and absorb any urine released by the animal. The filter paper is replaced at two-hour intervals across the eight-hour test day and inspected with UV light to visualize urine spots, which are easily distinguished from saliva, water, or fecal liquid spots due to fluorescence of urine under UV light. The number and area of the spots are measured. The area of the fluorescent spot is converted to volume using a conversion scale we empirically created (i.e. known volume of urine applied to paper=spot with area=x mm$^2$) that is accurate within 10% from 10 μl to 10 ml. For measurement of fecal incontinence, the absence or presence of feces is noted and weighed, if present.

On a weekly basis, amongst all animals in the group, the mean number of incontinence episodes (number of spots and/or presence of feces) and the mean volumes of incontinence (area of spots) and weight of feces are compared with, versus without, low frequency pudendal stimulation. For each week, differences in mean numbers and volumes/weights of episodes with, versus without, pudendal stimulation are examined for significance using a t-test. The number and volume/weight of incontinence episodes are plotted on a weekly basis across the eight-week study. Differences in weekly mean numbers and volumes/weights are assessed for significance using ANOVA followed by appropriate post-hoc testing to determine if the efficacy remains constant across time. Pudendal stimulation significantly reduces both the number and the volume/weight of incontinence episodes with no consistent changes in efficacy across the eight-week period.

C. Methods to Determine Effects on Voiding Dysfunction.

The same animals are used to determine effects on voiding dysfunction. On test days, the animals receive one of four treatments on a random schedule:
1) saline (1 ml/second),
2) saline+pudendal block (five minutes),
3) [Lys$^5$,MeLeu$^9$,Nle$^{10}$]-neurokinin A$_{(4-10)}$, or
4) [Lys$^5$,MeLeu$^9$,Nle$^{10}$]-neurokinin A$_{(4-10)}$+pudendal block (five min).

Voided volume (VV) and fecal weight is measured for ten minutes after treatment. After voided volume/weight is measured, on a randomized and blinded basis, residual volume (RV) is emptied from the bladder by Credé or Credé+pudendal block. Animals voiding by Credé alone will then receive Credé+pudendal block to see if more urine can be released. In this way, all animals will receive pudendal block on a daily basis (except weekends and holidays). VV and RV are used to calculate VE.

A neurokinin2 receptor agonist, e.g. [Lys$^5$,MeLeu$^9$,Nle$^{10}$]-neurokinin A$_{(4-10)}$ (Rupniak, et al., Naunyn Schmiedebergs Arch Pharmacol. 2018 March; 391(3):299-308), is administered at a single dose based on previous studies throughout the eight-week period. Prior to testing in awake, spinal animals; the dose is tested in healthy, naïve animals to confirm that the dose is well-tolerated in awake animals by starting at a dose $\frac{1}{10}^{th}$ and then $\frac{1}{3}^{rd}$ the final dose prior to the final dose. Based on extensive urodynamic and awake voiding studies in rats, dogs, and minipigs, the effective dose is between 3-100 μg/kg (subcutaneously, "s.c.") and the first sign of uncomfortable GI effects appear between 100-300 μg/kg s.c.

On a weekly basis, amongst all animals, mean VE is calculated and statistical significance determined using a t-test. Difficulty of Credé is evaluated on a 5-point scale by the person who applies Credé maneuver. For each week, statistical differences in mean VE and Credé difficulty with, versus without, pudendal block is assessed with a t-test. The mean VE and Credé difficulty are plotted on a weekly basis across the eight-week study. Differences in weekly mean VE and difficulty are assessed for significance using ANOVA followed by appropriate post-hoc testing. If it becomes obvious (and statistically significant) that Credé is subjectively much easier with pudendal block than without, then pudendal block will be used every time the bladder is emptied by Credé for the remainder of the eight-week period.

D. Anticipated Results.

Saline alone does not release any significant amount of urine across the eight weeks. Pudendal block alone (with saline control) releases small amounts of urine during the five-minute period of stimulation. [Lys$^5$,MeLeu$^9$,Nle$^{10}$]-neurokinin A$_{(4-10)}$ administration alone releases large volumes of urine (i.e. VE 50%) consistently across the eight-week period with no observable adverse events. [Lys$^5$,MeLeu$^9$,Nle$^{10}$]-neurokinin A$_{(4-10)}$ administration with pudendal block produces 100% VE without adverse effects consistently across the eight-week period.

Example 3. Clinical Studies

A. Implant of Pudendal Nerve Electrodes.

It has been shown that electrical stimulation of the pudendal nerve at low frequency (~10 Hz) inhibits neurogenic bladder contractions (Peters, 2010 Neurourol Urodyn. September 29(7):1267-71; Martens et al., 2011 J Urol. September 186(3):798-804; Peters K M et al., 2005, Neurourol Urodyn. 24(7):643-7), which can lead to urine leakage. Using the methods of implantation of the tined electrodes described therein, implantation of a Programmable Pulse Generator can be successfully completed in about 30 minutes. Cuff electrodes have not been implanted on the pudendal nerve, but it is reasonable to assume that surgical implantation time will be longer than 30 minutes but still reasonable compared to various other surgical procedures.

B. Void/Continence Positions.

Brief (between 1 and 20 minutes, e.g. 5, 10 or 15 minutes), high frequency stimulation blocks PUD. This block is applied whenever the patient or caregiver wishes to void, typically 4-6 times a day as the most practical approach.

When not in this "void mode", continuous (throughout life) stimulation of pudendal (PUD) nerve activity between voids prevents urinary incontinence. Low frequency stimulation to the pudendal efferent and afferent fibers, between 1 and 20 Hz, causes the sphincter to tonically contract and may inhibit the bladder, respectively. Those of skill in the art will recognize that being in one mode or the other is apt to be the normal form of operation but a brief gap of no stimulus during a changeover of modes may be tolerated.

As will be recognized by a person of skill in the art, characteristics of electrical pulse, including, without limitation, amplitude (pulse strength, referring to the magnitude or size of a signal voltage or current), voltage, amperage, duration, frequency, polarity, phase, relative timing and symmetry of positive and negative pulses in biphasic stimulation, and/or wave shape (e.g., square, sine, triangle, sawtooth, or variations or combinations thereof) may be varied in order to optimize results in any particular patient or class of patients. Patients may be classified by species, disease/condition, sex, or any other factor that can be generalized to a group.

C. Special Conditions.

Optionally, in the event that a patient becomes incapacitated and is unable to switch to voiding mode, the device is programmed to provide a warning signal (chosen by the patient, e.g. sound, light, and vibration) after a set time (e.g. 3 hours). This programming is done by the physician or the patient. If the individual does not address the warning and void within a preset time (e.g. 1 hour after warning), the device automatically switches to the Void Mode to prevent excessive pressure in the bladder and possible renal damage. While the consequent incontinent episode is not a desired outcome, it only occurs if the individual or the individual's caregiver has not responded to the warning. The warning can be sent wirelessly to the caregiver's phone or to an alarm. In a case where the patient is truly incapacitated, this result is not any different from what would happen naturally in such circumstances.

Optionally, in the event that the patient anticipates a temporary increase in abdominal pressure that might provoke the release of urine or feces (such as physical exertion associated with transfer from wheelchair to bed or a cough or sneeze), a trigger may be activated (by pressing a button or by a voice command) that increases the pudendal stimulation to provide temporary, powerful contraction of the external urethral and anal sphincter to resist the increase in abdominal pressure.

Optionally, the trigger may be activated automatically by sensors that detect the onset of abdominal pressure increases using pressure transducers or electrical activity of the pelvic or abdominal muscle EMG activity.

Stimulator Device.

Figure 5:
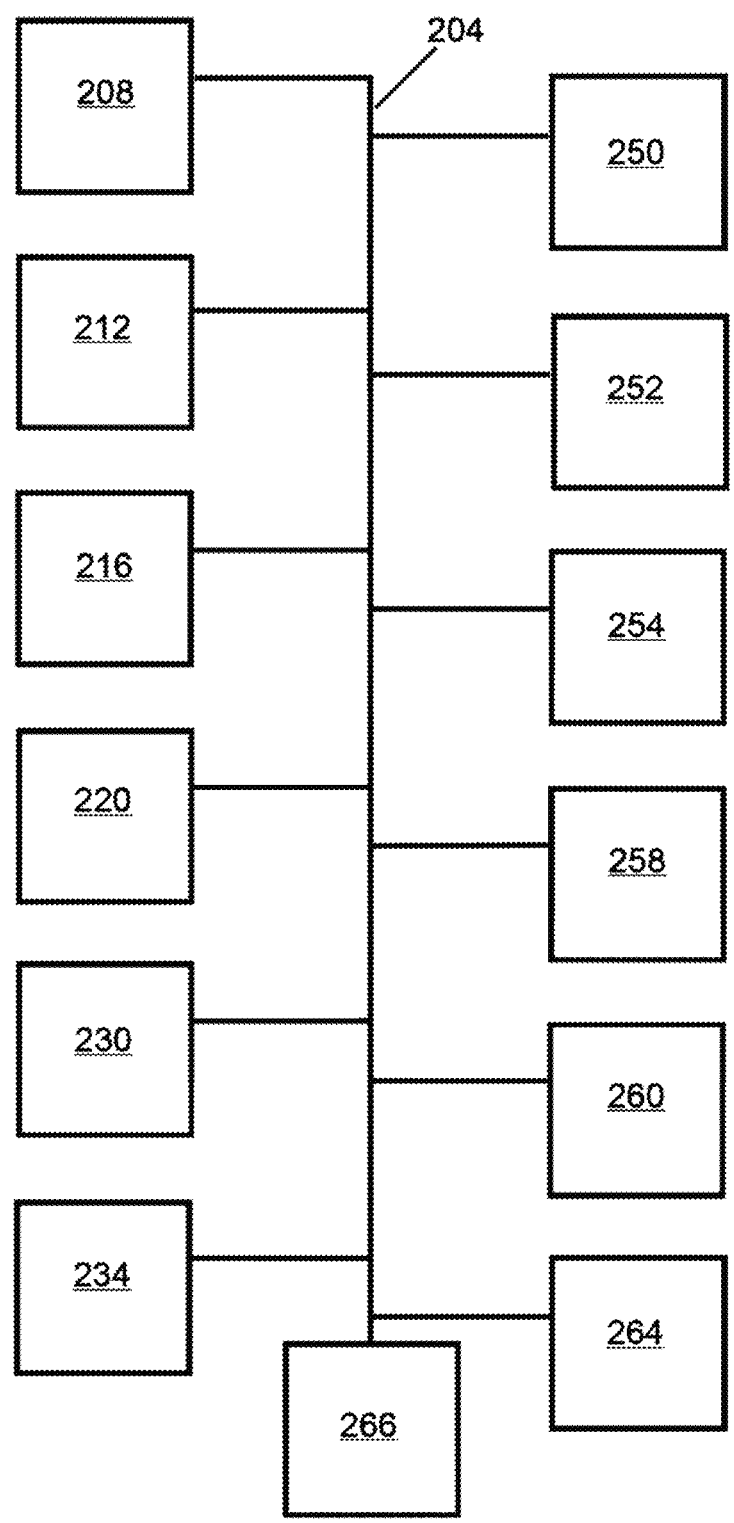
FIG. 5 sets forth the basic components of a stimulator device 200.

FIG. 5 sets forth the basic components of a stimulator device 200 that may be used in accordance with the teachings of the present disclosure. Those of skill in the art will recognize that this is not a detailed description of all components needed to make a complete device. For example, FIG. 5 does not include a power supply, but conventional aspects of a medical stimulator need not be conveyed to those of skill in the art. Likewise, conventional circuitry to limit electrical charge leakage and to provide for patient safety are assumed to be within the skill set of those of skill in the art and not detailed here.

The stimulator device 200 includes a set of one or more communication buses 204 to convey digital information from one component to another. There may be additional control signals conveyed to a specific component to provide a control signal to move from one mode to another. One of skill in the art will appreciate that some components of stimulator device 200 may be connected to other components by wireless rather than wired connections. For purposes of the simplified diagram of FIG. 5, the set of one or more communication buses 204 may be deemed to include such wireless links. The various wired and wireless links between components are conventional and design dependent and need not be shown here.

The stimulator device 200 will have one or more memory devices 208 where instructions for operation of the stimulator device 200 and possibly customized setting values are stored. The memory devices 208 may include volatile memory and non-volatile memory. Instructions may be stored as software, firmware, or other forms of storing instructions.

The memory devices 208 may be used by the stimulator device 200 to store a certain number of events for later analysis. Examples of the information stored may include the times that the modes were changed from store to void or void to store. Storing the times would allow noting of any unusual periods between void states. The memory devices 208 may store any pressure transients and the time of the transient that triggered a response from the stimulator device 200 as described below.

The stimulator device 200 may have one or more processors 212 to read and act upon instructions or inputs so as to implement the teachings of the present disclosure.

The stimulator device 200 is likely to have a first input device 216 for use by the end user to allow for change from a first stimulation mode promoting the storage of feces and urine to a second stimulation mode promoting the voiding of feces and urine.

The stimulator device 200 may have a second input device 220 or port for connection to a removable input device 220 to allow for more detailed interaction with the stimulator device 200. This may include work for initial setup of the stimulator device 200 to work effectively with the patient using the minimal stimulation levels for effective intervention. The detailed interaction may include providing software updates, checking event logs or other stored history, or other interactions known to be useful with a digital medical device.

Those of skill in the art will recognize that it is a design choice on how much of the tailoring of settings is left available to the end user and how much of the tailoring of settings is left for control by a medical specialist. This choice will impact the functionality provided for the end user interface and the first input device 216. Those of skill in the art will recognize that the stimulator device 200 may have a single input device 216 that serves to receive input from both the end user and the medical specialist.

The stimulator device 200 may have at least one communication port 230 to support wired communication between the stimulation device 200 and external devices such as memory, testing devices, or other components.

The stimulation device 200 may have at least one wireless communication transceiver 234 to allow wireless interaction with devices beyond the stimulation device 200. This functionality may be used to provide alerts to mobile phones associated with the patient/caregiver other family members, and health care providers. The format of the alerts may be text messages, emails, or voice messages as known in the art of alert systems. The wireless interaction may be with an alarm device located in the room or wheelchair of a patient to provide a visual or auditory alarm. Those of skill in the art will recognize that instead of a transceiver that can serve as both a transmitter and a receiver, some designs may be implemented just with a transmitter to send messages.

The stimulation device 200 may have at least two electrodes 250 and 252 for placement adjacent to each of the two pudendal nerves (104 FIG. 1). The same electrodes 250 and 252 may be used to provide both LFS and HFS. Those of skill in the art will recognize that one could implement that stimulation device 200 with one or more electrodes for use in applying the LFS and a separate set of one or more electrodes for applying the HFS. The electrodes 250 and 252 used to stimulate the nerves may be of any composition or mixture of compositions, such as platinum or stainless steel, as are appropriate for implantation in the patient, and may be of any configuration for stimulating nerves, including monopolar, bipolar, tripolar, or quadripolar with various placements of the anode(s) and cathode(s). (Bhadra N, Kilgore K L. High-frequency electrical conduction block of mammalian peripheral motor nerve. Muscle Nerve. 2005; 32:782-90).

The stimulation device 200 may have a pulse generator 254 for generating the LFS and HFS. A range of different stimulation sequences may be used for LFS as noted above in connection with the discussion of the various examples. While the frequency of the stimulation cycles may be relatively low (less than 50 Hz), the actual active pulses applied within the stimulation cycle may include stimulation at higher frequencies for short bursts as illustrated in FIG. 4.

A range of different stimulation sequences may be used for LFS as noted above in connection with the discussion of the various examples. The LFS and HFS may be adjustable on one or more parameters or they may be preset values that cannot be adjusted by the patient/caregiver. Those of skill in the art will recognize that a stored sample of LFS or HFS could be sent repetitively to the electrode instead of generating the stimulus with a pulse generator 254.

The pulse generator 254 may be implantable. Implantable pulse generators are known in the art and can be licensed or purchased or built based on existing devices known to deliver LFS and HFS pulses that meet the pulse parameters of the current invention (Nexeon, Dallas, Tex.; ReShape, San Clemente, Calif.; Nuvectra, Plano, Tex.; Minnetronix, St. Paul, Minn.). These generators may further comprise wireless communication systems configured to send control instructions to the implantable pulse generator.

The stimulating device 200 may include a timer 258. As noted above, the stimulating device 200 may be configured to switch from storage mode (LFS) to void mode (HFS) after a prescribed time interval. The stimulating device 200 may provide a reminder to the patient/caregiver of the upcoming switch in modes.

The timer 258 may also be used to maintain a running time since the last void cycle so that if the patient/caregiver did not execute a manual request for a void cycle within a clinically reasonable period of time, various steps of increasing severity may be taken. The steps may be providing reminders to the patient/caregiver, providing reminders to other parties, and contacting a health care provider to alert the health care provider that material has not been voided within a prescribed period of time. There may be other actions depending on the programming of the stimulating device 200.

The stimulating device 200 may have a urinary pressure sensing device 260 implanted in the bladder. The stimulating device 200 may have a fecal pressure sensing device 264 implanted in the rectum or abdomen. The urinary pressure sensing device 260 and the fecal pressure sensing device 264 may communicate wirelessly with the stimulating device 200. An example of a wireless implantable bladder pressure monitor is shown at aptcenter.research.va.gov/programs/health-and-monitoring/bladder-pressure-monitor/(www prefix omitted).

The stimulating device 200 may be programmed to respond to an excess of pressure detected by one of the pressure sensing devices 260 or 264 by altering the LFS to provide a higher level of stimulation to cause a higher level of sphincter contraction in the external urethral sphincter 134 in the urethra 138 and in the external anal sphincter 124 in the anal canal 128. The higher level of stimulation is likely to be for a limited time period to overcome a temporary increase in pressure. The spike in pressure that is meant to be opposed by an increase in sphincter contraction may come from exercise or transfers from wheelchair to bed or vice versa. The spike in pressure could come from sneezing or coughing.

The stimulating device 200 may be programmed to respond to an end user command via user I/O device 266 to allow for temporary increases in the output of the stimulus pulses. The end user command may be initiated by interacting with any known and appropriate user I/O device 266 such as activating a remote control button or by remote control voice command. The higher level of stimulation is likely to be for a limited time period in anticipation of a temporary increase in pressure. The anticipation of elevated pressure may come from anticipation of exercise or transfers from wheelchair to bed or vice versa or in anticipation of a sneeze or cough.

It is expected that this user I/O device 266 will be a simple interface for quick input in contrast with the more comprehensive first input device 216 that may be used by the end user to modify the operation of the device. Those of skill in the art will appreciate that the functionality of the user I/O device 266 could be folded into the first input device 216 so that the device does not have a distinct I/O device for this use.

The stimulating device 200 may be programmed to respond to an extended, and potentially damaging, excess of pressure detected by one of the pressure sensing devices 260 or 264 by altering the LFS to switch from LFS to HFS to relax the external urethral sphincter 134 in the urethra 138 and the external anal sphincter 124 in the anal canal 128 to prevent bladder or renal damage due to episodic or prolonged pathological pressure increases pressure. While the precise settings for a particular patient may be set by the medical professional responsible for this patient, a pressure in excess of 80 mm Hg (about 109 cm of H20) for more than ten minutes may be deemed a trigger to take action.

The stimulating device 200 may communicate warnings after a shorter period of elevated pressure such as at 5 minutes, 7 minutes, and 9 minutes before switching to void mode without a user input requesting a switch to void mode. The stimulating device 200 may have a way for an end user to delay the switch to void mode for a few minutes if a few extra minutes are desired to get to a bathroom. The stimulating device 200 may be set to alert a medical provider if the delay request is made. This alert may prompt the medical provider to contact the end user to check on the status and ensure that a void will occur promptly. If the end user cannot be reached, the medical provider may have the ability to force the switch to void mode overriding the end user request for a delay. Likewise, the ability to obtain a delay may be overridden by the stimulating device 200 or the medical provider if the measured pressure gets to an unacceptable level such as 200 mm Hg.

Process of Use.

Figure 6:
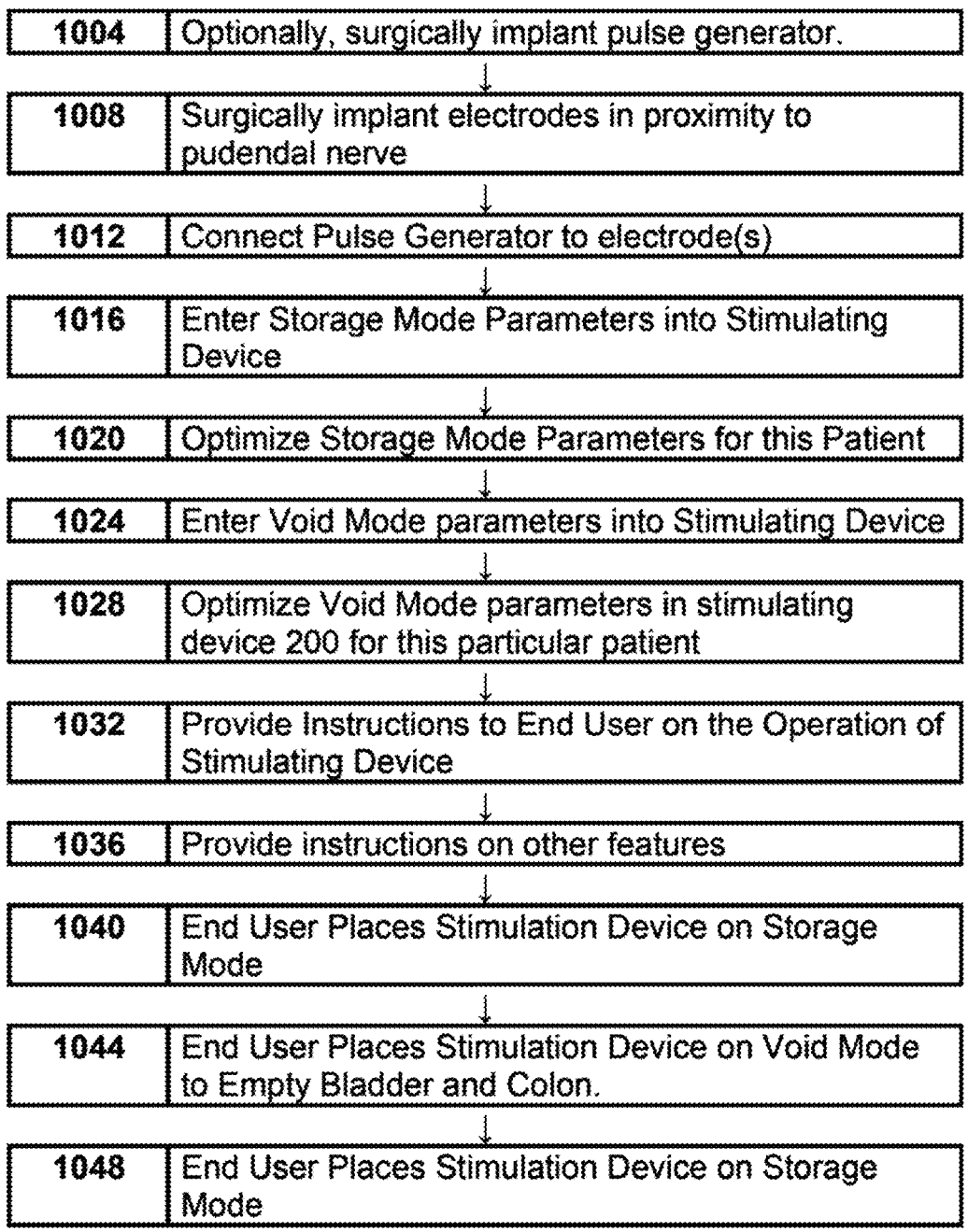
FIG. 6 is a high-level flowchart of a process 1000 for one use of the teachings of the present disclosure.

FIG. 6 is a high-level flowchart of a process 1000 for one use of the teachings of the present disclosure.

Step 1004—Optionally, surgically implant pulse generator 254. The surgical implantation can be done in accordance with methods known in the art. While there are advantages of having the pulse generator 254 implanted along with the electrodes 250, this is not strictly required and the electrodes 250 may be controlled by the pulse generator 254 through a wired connection that traverses the skin of the patient or through a short-range wireless connection as known in the art. One could also temporarily implant the electrodes and test the clinical benefit of the stimulation for the patient prior to a permanent implantation of the pulse generator as is routinely done for various nerve stimulation devices.

Step 1008—Surgically implant electrodes in proximity to pudendal nerve efferent and afferent axons. Those of skill in the art will recognize the requisite proximity to provide stimulation at a lower level of stimulation to conserve battery life and so that the stimulation does not have additional unintended consequences.

Step 1012—Connect pulse generator to electrodes.

Step 1016—Enter storage mode parameters into stimulating device 200. Those of skill in the art will appreciate that the storage mode parameters may be preset for a given class of patient before implantation and then adjusted as needed.

Step 1020—Optimize storage mode parameters for this patient.

Step 1024—Enter voiding mode parameters into stimulating device 200. Those of skill in the art will appreciate that an initial estimate of voiding mode parameters may have been programmed into the stimulating device 200 before implantation.

Step 1028—Optimize voiding mode parameters in stimulating device 200 for this particular patient.

Note that while it is likely that the storage mode parameters may be entered and optimized before the voiding mode parameters, this is not a strict requirement.

The process of optimizing the storage mode and voiding mode parameters may be done in any clinically expedient manner. The process may be as elaborate as set forth in the animal studies described above. Alternatively, the physician could insert a finger in the rectum when the LFS is applied. The physician would then adjust stimulation parameters for LFS within the ranges deemed safe and effective. The physician or an assistant would sense the external anal sphincter contractions on the inserted finger or record it with a pressure-sensing balloon and note whether a particular change increased the strength of the contraction, decreased the strength of the contraction, or had no impact on the strength of the contraction. The goal is to find a way to minimize the total amount of electrical charge used without losing contraction strength.

The voiding mode parameters can be optimized by applying HFS which should cause the external anal sphincter to relax. The adequacy of the HFS can be tested by testing for the bulbospongiosus reflex and not sensing a contraction of the external anal sphincter in response to the stimulus to test for the bulbospongiosus reflex.

Note while the animal studies separately tested the external urethral sphincter 134 (FIG. 1), one practiced in the art recognizes that the adjustments can be made using just the external anal sphincter 124 as the external urethral sphincter 134 should behave in a substantially corresponding manner to the external anal sphincter 124.

Optionally, the optimization process may be repeated after a few weeks, as the tissue healing may change the resistance to the stimulation current from the electrode. Thus, a patient may come back at two weeks, four weeks, three months, six months, and at one year to make additional refinements in the stimulation to seek the minimal stimulation that provides optimal results.

Step 1032—Provide instructions to patient or caregiver on the operation of stimulating device 200 and the input device to control the stimulating device 200. Those of skill in the art will appreciate that some instruction can be provided before the stimulating device 200 is implanted and tuned to the particular patient.

Step 1036—Instruct end user (patient or caregiver) to control the other features of stimulating device 200. Examples of these additional features include setting maximum time interval between void periods before alarms are sent out. The patient and caregiver may want to input the contact information for the parties that receive alerts or warnings if the time interval between void periods extends beyond various thresholds. The stimulating device 200 may be programmed to automatically switch to void mode after a certain time interval which may cause the patient to soil clothing but will prevent the risk of harm to the patient. The stimulating device may be programmed to increase or modify stimulation parameters when temporary increases in abdominal pressure or EMG activity are detected. The stimulating device may be programmed to respond to end user commands via user I/O device 266 to increase or modify the strength of the stimulation. The user input may call for a temporary increase or a longer term modification.

Step 1040—End user (patient or caregiver) places the stimulator device in store mode which provides LFS to help hold urine in the bladder and feces in the colon.

Step 1044—Patient places stimulator device in void mode which stops providing LFS and starts providing HFS to assist the patient in discharging urine to empty the bladder and to discharge feces to empty the colon. Note that the voiding of the bladder or colon may be enhanced by providing the patient with a dose of bladder or colon smooth muscle prokinetic agent such as a neurokinin2 receptor agonist to complement the work of the HFS. The prokinetic agent can be provided in any of a number of fast-acting forms known to those of skill in the art including nasal injection, sublingual application, and subcutaneous application.

Step 1048—Patient places stimulator device back into store mode to again provide LFS to help hold urine in the bladder and feces in the colon.

ALTERNATIVES AND VARIATIONS

Only LFS Stimulation to Assist with Holding.

While the example set forth above provided both LFS stimulation 194 and HFS stimulation 198 in order to assist with holding and voiding material, certain patients may benefit from a stimulating device that performs only LFS stimulation 194 to assist with continence. These patients may benefit from a stimulation device that provides only LFS stimulation 194 and is inactive when the patient seeks to void.

Figure 17:
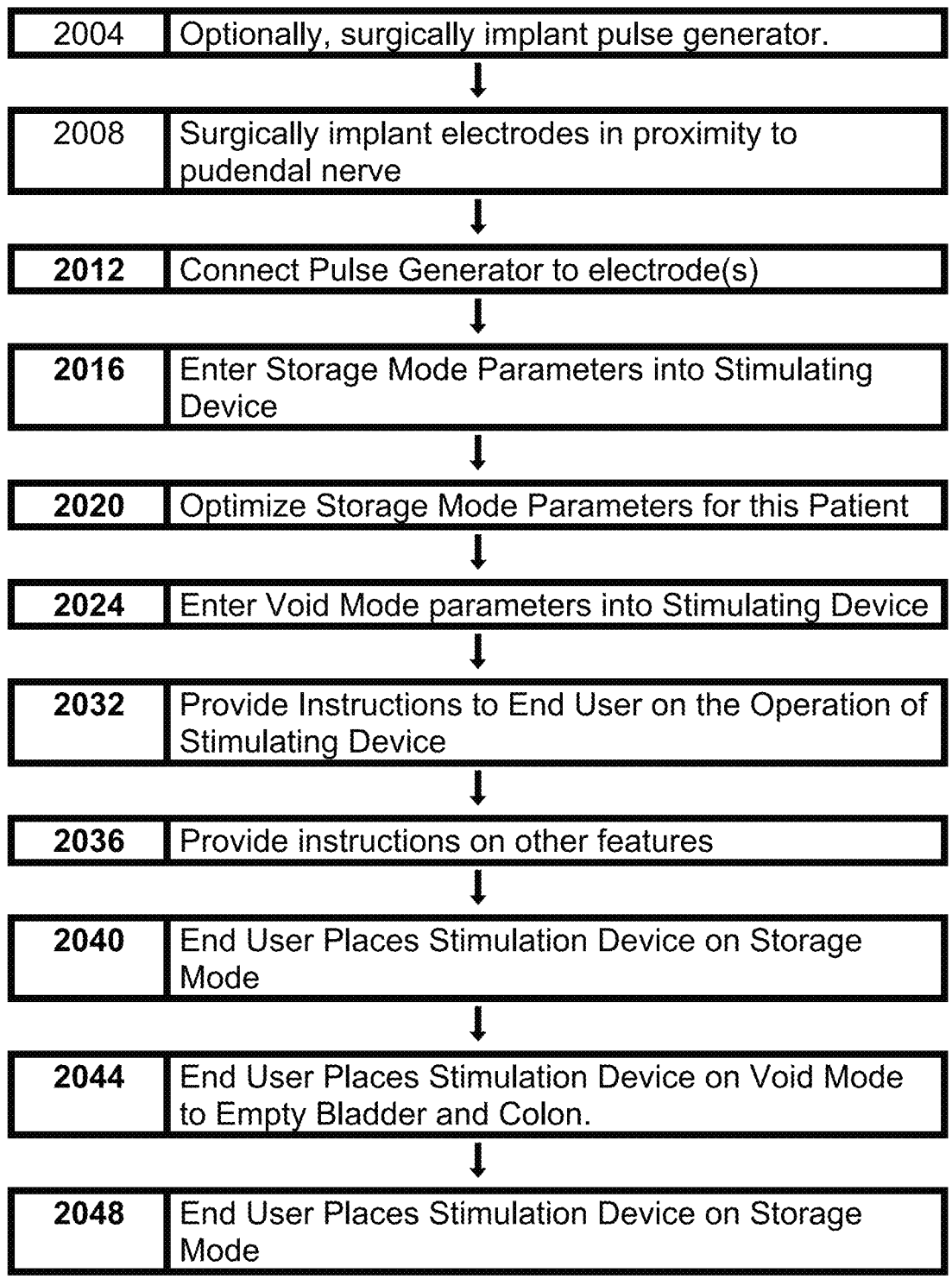
FIG. 17 is a high-level flowchart of a process 2000 for one use of the teachings of the present disclosure.

FIG. 17 is a high-level flowchart of a process 2000 for one use of the teachings of the present disclosure. This flowchart is almost identical to FIG. 6 discussed above. Likewise the text that follows is almost identical to the text describing the process 1000. A difference is that the Void mode is simply a cessation of the Storage mode stimulus and not the application of HFS to block nerve impulses from the external anal sphincter and the external urethral sphincter.

Step 2004—Optionally, surgically implant pulse generator 254. The surgical implantation can be done in accordance with methods known in the art. While there are advantages of having the pulse generator 254 implanted along with the electrodes 250, this is not strictly required and the electrodes 250 may be controlled by the pulse generator 254 through a wired connection that traverses the skin of the patient or through a short-range wireless connection as known in the art. One could also temporarily implant the electrodes and test the clinical benefit of the stimulation for the patient prior to a permanent implantation of the pulse generator as is routinely done for various nerve stimulation devices.

Step 2008—Surgically implant electrodes in proximity to pudendal nerve efferent and afferent axons. Those of skill in the art will recognize the requisite proximity to provide stimulation at a lower level of stimulation to conserve battery life and so that the stimulation does not have additional unintended consequences.

Step 2012—Connect pulse generator to electrodes.

Step 2016—Enter store mode parameters into stimulating device 200. Those of skill in the art will appreciate that the store mode parameters may be preset for a given class of patient before implantation and then adjusted as needed.

Step 2020—Optimize store mode parameters for this patient.

Step 2024—Enter voiding mode parameters into stimulating device 200. In this instance the voiding mode is simply the cessation of the store mode stimulation. Thus, there is not a need to optimize the void mode parameters.

Those of skill in the art will appreciate that the stimulation device may be made without the capacity to serve as a dual mode stimulation device (LFS and HFS). Alternatively, a dual-mode device may be used in a single-mode use (just LFS) by programming the stimulating device. Those of skill in the art will appreciate that an initial estimate of voiding mode parameters may have been programmed into the stimulating device 200 before implantation.

Note that while it is likely that the store mode parameters may be entered and optimized before the voiding mode parameters, this is not a strict requirement.

Note that while it is likely that the store mode parameters may be entered and optimized before the voiding mode parameters, this is not a strict requirement.

The process of optimizing the store mode may be done in any clinically expedient manner. The process may be as elaborate as set forth in the animal studies described above. Alternatively, the physician could insert a finger in the rectum when the LFS is applied. The physician would then adjust stimulation parameters for LFS within the ranges deemed safe and effective. The physician or an assistant would sense the external anal sphincter contractions on the inserted finger or record it with a pressure-sensing balloon and note whether a particular change increased the strength of the contraction, decreased the strength of the contraction, or had no impact on the strength of the contraction. The goal is to find a way to minimize the total amount of electrical charge used without losing contraction strength.

Note while the animal studies separately tested the external urethral sphincter 134 (FIG. 1), one practiced in the art recognizes that the adjustments can be made using just the external anal sphincter 124 as the external urethral sphincter 134 should behave in a substantially corresponding manner to the external anal sphincter 124.

Optionally, the optimization process may be repeated after a few weeks, as the tissue healing may change the resistance to the stimulation current from the electrode. Thus, a patient may come back at two weeks, four weeks, three months, six months, and at one year to make additional refinements in the stimulation to seek the minimal stimulation that provides optimal results.

Step 2032—Provide instructions to patient or caregiver on the operation of stimulating device 200 and the input device to control the stimulating device 200. Those of skill in the art will appreciate that some instruction can be provided before the stimulating device 200 is implanted and tuned to the particular patient.

Step 2036—Instruct end user (patient or caregiver) to control the other features of stimulating device 200. Examples of these additional features include setting maximum time interval between void periods before alarms are sent out. The patient and caregiver may want to input the contact information for the parties that receive alerts or warnings if the time interval between void periods extends beyond various thresholds. The stimulating device 200 may be programmed to automatically switch to void mode after a certain time interval which may cause the patient to soil clothing but will prevent the risk of harm to the patient. The stimulating device may be programmed to increase or modify stimulation parameters when temporary increases in abdominal pressure or EMG activity are detected or when requested by an end-user. The stimulating device may be programmed to respond to end user commands via user I/O device 266 to increase or modify the strength of the stimulation. The user input may call for a temporary increase or a longer term modification.

Step 2040—End user (patient or caregiver) places the stimulator device in store mode which provides LFS to help hold urine in the bladder and feces in the colon.

Step 2044—Patient places stimulator device in void mode which stops providing LFS to allow the patient to discharge urine to empty the bladder and to discharge feces to empty the colon. Note that the voiding of the bladder or colon may be enhanced by providing the patient with a dose of bladder or colon smooth muscle prokinetic agent such as a neurokinin2 receptor agonist. The prokinetic agent can be provided in any of a number of fast-acting forms known to those of skill in the art including nasal injection, sublingual application, and subcutaneous application.

Step 2048—Patient places stimulator device back into store mode to again provide LFS to help hold urine in the bladder and feces in the colon.

Only HFS Stimulation to Assist with Voiding.

Certain patients may benefit solely from HFS stimulation 198 to assist with voiding by blocking action potentials from sphincter efferent motor neurons in order to preclude sphincter dyssynergia and thus keep the external anal sphincter 124 and the external urethral sphincter 134 relaxed and open. The voiding process may be driven by the patient exerting control over the bladder 136 or colon 126 or may be assisted by a fast-acting drug to help contract the bladder 136 or colon 126. These patients may not need any assistance to promote continence and the stimulating device may be idle between periods of applied HFS stimulation 198.

Use of Direct Current (DC) to Stimulate or Block the Pudendal Nerve.

Those of skill in the art will appreciate that application of direct current (DC) pulses can elicit action potentials in peripheral nerves and that gradually increasing DC application can block conduction of action potentials in peripheral nerves. While use of DC electrodes has not been widely applied clinically in humans due to concerns of toxicity from electrochemical reactions occurring at the metal-tissue interface, one could theoretically use electrodes that provide DC to stimulate or block the pudendal nerves as described in this patent.

Single-Mode Operation of Dual-Mode Device.

Those of skill in the art will appreciate that a single-mode device (LFS or HFS) may be made without the capacity to serve as a dual mode (LFS and HFS). Alternatively, a dual-mode device may be used in a single-mode use (just LFS or just HFS) by programming the stimulating device.

Single Sphincter Stimulation.

While the examples set forth above provided stimulation control to both the external anal sphincter and the external ureteral sphincter and ideally provided some stimulation control to the bladder, one could locate the electrodes distally on the pudendal nerve branches to target just the external anal sphincter or just the external urethral sphincter using LFS and HFS as described above. Thus, a patient may receive four electrodes, two on the branches of the pudendal nerves servicing the external urethral sphincter and two electrodes on the branches of the pudendal nerves servicing the external anal sphincter.

If the electrodes were placed after the relevant split in the pudendal nerve so that stimulation from one pair of electrodes only impacts the external urethral sphincter and stimulation from another pair of electrodes impacts the external anal sphincter, then the responses to spikes in pressure detected by the pressure sensor can be targeted to one sphincter or the other. Thus, the stimulating device 200 may react to a pressure spike received at the urinary pressure sensing device 260 implanted in the bladder by providing stimulation to help provide extra closing force only to the external urethral sphincter 134. Likewise, the stimulating device 200 may react to a pressure spike received at the fecal pressure sensing device 264 implanted in the rectum or abdomen by providing stimulation to help provide extra closing force only to the external anal sphincter 124.

Separate Electrode for Pudendal Afferent Fibers to Control Bladder.

An additional electrode could be placed to specifically interact with pudendal afferent nerves to relax the bladder during storage mode (may also be called hold mode). The same electrode can be used to contract the bladder during void mode. This electrode placement would not impact sphincter contraction of either the external urethral sphincter 134 or the external anal sphincter 124. The stimulation to cause contraction may be a third type of stimulation optimized to stimulate contractions and different from the second type of stimulation being used to prevent sphincter dyssynergia.

Separate Electrode for Pudendal Afferent Fibers to Control Colon.

An additional electrode could be placed to specifically interact with pudendal afferent nerves to relax the colon during storage mode (may also be called hold mode). The same electrode can be used to contract the colon during void mode. This electrode placement would not impact sphincter contraction of either the external urethral sphincter 134 or the external anal sphincter 124. The stimulation to cause contraction may be a third type of stimulation optimized to stimulate contractions and different from the second type of stimulation being used to prevent sphincter dyssynergia Unilateral Stimulation.

The discussion provided above assumed bilateral stimulation; that is stimulation to the relevant portion of the pudendal nerve on both the right and left side of the body. While this is apt to be the most common solution, nothing in this disclosure should be read to exclude unilateral stimulation of the pudendal nerve by one or more electrodes on a single side of the body. Such a solution may be appropriate when a patient has experienced unilateral damage to the nervous system and does not need stimulation to both the right and left pudendal nerves.

Induced Temporary Increases in Contraction Pressure.

As noted above, during brief periods of exertion that result in elevation of abdominal pressure (and subsequently pressure transferred to the bladder and rectum), such as in anticipation of a cough or sneeze or exercise or a transfer from bed to wheelchair and back, it is practical to increase the urethral or anal contraction pressures, possibly to their maximal force, for those brief periods of time.

The trigger to increase external sphincter force and possibly move to maximum force could be one or more of the following:

A user-activated button, including a portion of an input screen that serves as a button;

A voice command;

An electrical signal from the abdominal, pelvic, or anal sphincter muscles indicating muscle contraction; and An electrical signal from a pressure transducer recording abdominal, bladder, or rectal pressure.

Those of skill in the art will appreciate that more than one trigger may be used so as to be responsive to a variety of unplanned events (such as a cough or sneeze) and planned events such as a move from wheelchair to bed.

Induced Cessation and Reactivation of LFS.

During periods when leakage of waste is not a concern (e.g. during sleep), it is practical to turn the stimulator off completely (cessation) to conserve battery charge and turn it on when needed (reactivation).

The trigger to turn the stimulator off could be one or more of the following:
- A user-activated button, including a portion of an input screen that serves as a button; and
- A voice command.

The trigger to turn the stimulator on (re-activate the stimulator) could be one of the following:
- A user-activated button, including a portion of an input screen that serves as a button;
- A voice command;
- An electrical signal from the abdominal, pelvic, or anal sphincter muscles indicating muscle contraction; and
- An electrical signal from a pressure transducer recording abdominal, bladder, or rectal pressure.

Those of skill in the art will appreciate that more than one trigger may be used to turn the stimulator on so as to be responsive to a variety of unplanned events (such as a cough or sneeze) and planned events such as a move from bed to wheelchair upon wakening.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

Where methods and/or events described above indicate certain events and/or procedures occurring in a certain order, the ordering of certain events and/or procedures may be modified. Additionally, certain events and/or procedures may be performed concurrently in a parallel process when possible, as well as performed sequentially as described above.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A method of treating urinary and fecal incontinence by providing control to at least one end user of storage and voiding of urine and feces for a patient; the method comprising:
   placing a pair of electrodes in proximity to a left pudendal nerve and a right pudendal nerve of the patient to provide bilateral stimulation to the pudendal nerves;
   placing the pair of electrodes in communication with a control system that can selectively convey stimulation to the pair of electrodes;
   receiving a selection of "Store" from at least one end user;
   reacting to the received selection of "Store" by starting application of a first stimulation to the pair of electrodes;
   the first stimulation adapted to bilaterally generate action potentials in efferent motor nerves to directly promote concurrent sustained contractions of both:
      an external urethral sphincter to preclude a release of urine from the external urethral sphincter; and
      an external anal sphincter to preclude a release of feces from the external anal sphincter;
   maintaining the first stimulation to produce the sustained contractions for a duration of at least ten minutes;
   receiving a selection of "Void" from at least one end user;
   reacting to the received selection of "Void" by ceasing application of the first stimulation to the pair of electrodes;
   ceasing application of the first stimulation allowing relaxation of:
      an external urethral sphincter to allow voiding of urine through the external urethral sphincter; and
      an external anal sphincter to allow voiding of feces through the external anal sphincter;
   receiving another selection of "Store" from at least one end user; and
   reacting to the received another selection of "Store" by resuming application of the first stimulation to the pair of electrodes.

2. The method of claim 1 wherein the at least one end user includes the patient.

3. The method of claim 1 wherein the first stimulation is continuously provided to the pair of electrodes for over two hours to promote concurrent contraction of both:
   the external urethral sphincter to preclude the release of urine from the external urethral sphincter; and
   the external anal sphincter and to preclude the release of feces from the external anal sphincter.

4. The method of claim 1 wherein the first stimulation applies a set of trains of stimulation pulses and a frequency of stimulation pulses within each train is not more than 50 Hz.

5. The method of claim 1 wherein the application of the first stimulation to the pair of electrodes also causes relaxation of a bladder.

6. The method of claim 1 wherein the application of the first stimulation to the pair of electrodes also causes contractions of a bladder but the contraction of the external urethral sphincter is sufficient to preclude the release of urine.

7. The method of claim 1 further comprising:
   monitoring a urinary pressure sensing device; and
   while applying the first stimulation to the pair of electrodes—responding to a detection of elevated pressure measured by the urinary pressure sensing device by changing the first stimulation to provide for an enhanced level of contraction of at least the external urethral sphincter for a duration of time.

8. The method of claim 1 further comprising:
   monitoring an abdominal pressure sensing device; and
   while applying the first stimulation to the pair of electrodes—responding to a detection of elevated pressure measured by the abdominal pressure sensing device by changing the first stimulation to provide for a period of time an enhanced level of contraction of:
      the external urethral sphincter to preclude the release of urine from the external urethral sphincter; and
      the external anal sphincter and to preclude the release of feces from the external anal sphincter.

9. The method of claim 1 further comprising:
   monitoring an abdominal muscle contractionسensing device; and
   while applying the first stimulation to the pair of electrodes—responding to a detection of muscle contraction by the abdominal muscle contraction sensing device by changing the first stimulation to provide for a period of time an enhanced level of contraction of:
      the external urethral sphincter to preclude the release of urine from the external urethral sphincter; and the external anal sphincter and to preclude the release of feces from the external anal sphincter.

10. The method of claim 1 wherein at least one end user provides an input via an input device to change the first stimulation to provide for an enhanced level of contraction of:
the external urethral sphincter; and
the external anal sphincter.

11. The method of claim 1 further comprising responding to an indication of elevated muscle contraction in a monitored muscle by changing the first stimulation to provide for an enhanced level of contraction of:
the external urethral sphincter; and
the external anal sphincter.

12. The method of claim 1 further comprising transmitting a warning after applying the first stimulation in excess of a first prescribed time duration value.

13. The method of claim 12 wherein the warning goes to an indicator device in proximity to the patient.

14. The method of claim 12 wherein the warning goes to a communication network to convey a message indicating application of the first stimulation in excess of the first prescribed time duration value.

15. The method of claim 12 wherein after a second continuous time period of applying the first stimulation in excess of a second prescribed time duration value, longer than the first prescribed time duration value, the control system reacts by:
ceasing application of the first stimulation without receipt of the selection of "Void" from at least one end user.

16. The method of claim 1 wherein while applying the first stimulation to the pair of electrodes,
the control system monitors a timer and when the timer indicates a first continuous time period of applying the first stimulation in excess of a first prescribed time duration value—the control system reacts by transmission of a first warning message to a first set of recipients and
the control system continues to monitor the timer and when the timer indicates a longer continuous time period of applying the first stimulation in excess of a second prescribed time duration value, longer than the first prescribed time duration value—the control system reacts by sending a second warning message to a second set of recipients, larger than the first set of recipients.

17. The method of claim 1 further comprising testing a patient's response to the first stimulation applied to the pair of electrodes to adjust parameters of the first stimulation to provide a strong contraction to a particular sphincter while seeking to minimize a total amount of electrical charge applied to the patient per unit of time receiving the first stimulation.

18. The method of claim 17 wherein the testing the patient's response to the first stimulation is conducted using the external anal sphincter.

19. The method of claim 1 further comprising
receiving a selection of sleep from at least one end user to enter sleep mode; and
reacting to the selection of "sleep" by ceasing all application of stimulation to the pair of electrodes.

20. The method of claim 19 wherein during sleep mode the control system responds to a trigger to resume the application of the first stimulation to the pair of electrodes.

21. The method of claim 1 wherein in addition to reacting to received selection of "Void" by ceasing application of the first stimulation to the pair of electrodes,
the method further comprises reacting to the received selection of "Void" by starting application of a second stimulation, different from the first stimulation, to the pair of electrodes;
the second stimulation adapted to block nerve signals that would interfere with:
the release of urine from the external urethral sphincter; and
the release of feces from the external anal sphincter.

22. The method of claim 21 wherein the second stimulation uses a stimulation that is charge balanced and provided at a continuous duty cycle at a frequency not less than 1 kHz.

23. The method of claim 21 wherein the patient is provided with a prokinetic agent to assist in voiding.

24. The method of claim 23 wherein the prokinetic agent is a neurokinin2 receptor agonist.

25. The method of claim 21 wherein the control system may be configured to:
respond to the received selection of "Void" by ceasing the application of the first stimulation to the pair of electrodes without starting the application of the second stimulation; and
the control system may be subsequently configured to respond to the received selection of "Void" by ceasing the application of the first stimulation to the pair of electrodes and also starting the application of the second stimulation.

26. The method of claim 1 wherein all electrodes used to provide various forms of stimulation are used to emit stimulation that is identical for all electrodes.

27. A method of treating urinary and fecal incontinence by providing to at least one end user, control of storage and voiding of urine and feces for a patient; the method comprising:
placing of a pair of electrodes with one electrode in proximity to a left pudendal nerve of the patient and another electrode placed in proximity to a right pudendal nerve of the patient; and
placing a pulse generator adapted to provide pulses that bilaterally generate action potentials in pudendal efferent motor nerves through the pair of electrodes;
responding to a user input of "Store" by using the pulse generator to provide pulses that bilaterally generate action potentials in pudendal efferent motor nerves through the pair of electrodes to produce sustained contractions for a duration of at least ten minutes of:
a left side of an external urethral sphincter; and
a right side of the external urethral sphincter so as to prevent an escape of urine; and
a left side of an external anal sphincter; and
a right side of the external anal sphincter so as to prevent an escape of fecal matter.

28. The method of claim 27 wherein the pulses applied bilaterally to the pudendal nerve through the pair of electrodes simultaneously stimulates pudendal nerve afferent nerves to inhibit contraction of a urinary bladder.

29. The method of claim 27 wherein the at least one end user can select a "Void" command for the pulse generator, which will cause the pulse generator to stop providing the pulses that bilaterally generate action potentials in pudendal efferent motor nerves through the pair of electrodes.

30. The method of claim 27 wherein the at least one end user can select a "Void" command for the pulse generator, which will cause the pulse generator to:
1) stop providing the pulses that bilaterally generate action potentials in pudendal efferent motor nerves through the pair of electrodes; and
2) start delivering high frequency pulses in excess of 5 kHz that block pudendal efferent nerves from conducting action potentials from pudendal efferent motor neuron cell bodies in a spinal cord of the patient.

31. The method of claim 27 wherein the at least one end user includes the patient having issues with urinary and fecal incontinence.

32. A method of treating urinary and fecal incontinence by providing control to at least one end user of storage and voiding of urine and feces for a patient;
the method comprising:
placing a pair of electrodes in proximity to a left pudendal nerve and a right pudendal nerve of the patient to provide bilateral stimulation to the pudendal nerves;
placing the pair of electrodes in communication with a control system that can selectively convey stimulation to the pair of electrodes;
receiving a selection of "Store" from at least one end user;
reacting to the received selection of "Store" by starting application of a first stimulation to the pair of electrodes;
the first stimulation adapted to bilaterally generate action potentials in efferent motor nerves to directly promote concurrent sustained contractions constriction of both:
an external urethral sphincter to preclude a release of urine from the external urethral sphincter; and
an external anal sphincter to preclude a release of feces from the external anal sphincter;
receiving a selection of "Void" from at least one end user;
reacting to the received selection of "Void" by ceasing application of the first stimulation to the pair of electrodes;
ceasing application of the first stimulation allowing relaxation of:
an external urethral sphincter to allow voiding of urine through the external urethral sphincter; and
an external anal sphincter to allow voiding of feces through the external anal sphincter;
receiving another selection of "Store" from at least one end user; and
reacting to the received another selection of "Store" by resuming application of the first stimulation to the pair of electrodes;
the method further comprising:
monitoring a fecal pressure sensing device; and
while applying the first stimulation to the pair of electrodes—responding to a detection of elevated pressure measured by the fecal pressure sensing device by changing the first stimulation to provide for an enhanced level of contraction of at least the external anal sphincter for a period of time.

33. A method of treating urinary and fecal incontinence by providing control to at least one end user of storage and voiding of urine and feces for a patient;
the method comprising:
placing a pair of electrodes in proximity to a left pudendal nerve and a right pudendal nerve of the patient to provide bilateral stimulation to the pudendal nerves;
placing the pair of electrodes in communication with a control system that can selectively convey stimulation to the pair of electrodes;
receiving a selection of "Store" from at least one end user;
reacting to the received selection of "Store" by starting application of a first stimulation to the pair of electrodes;
the first stimulation adapted to bilaterally generate action potentials in efferent motor nerves to directly promote concurrent sustained contractions of both:
an external urethral sphincter to preclude a release of urine from the external urethral sphincter; and
an external anal sphincter to preclude a release of feces from the external anal sphincter;
receiving a selection of "Void" from at least one end user;
reacting to the received selection of "Void" by ceasing application of the first stimulation to the pair of electrodes;
ceasing application of the first stimulation allowing relaxation of:
an external urethral sphincter to allow voiding of urine through the external urethral sphincter; and
an external anal sphincter to allow voiding of feces through the external anal sphincter;
receiving another selection of "Store" from at least one end user; and
reacting to the received another selection of "Store" by resuming application of the first stimulation to the pair of electrodes;
the method further comprising:
monitoring a urinary pressure sensing device; and
while applying the first stimulation to the pair of electrodes—responding to a detection of prolonged period of elevated pressure by the urinary pressure sensing device by:
ceasing application of the first stimulation without waiting for receipt of the selection of "Void" from at least one end user.

34. A method of providing control to an end user of a patient's storage and voiding of waste; the method comprising:
placing a pair of electrodes with each electrode in proximity to a pudendal nerve containing:
efferent nerves for an external urethral sphincter and an external anal sphincter; and
afferent nerves controlling a bladder and a colon;
placing the pair of electrodes in communication with a control system that can selectively convey stimulation to the pair of electrodes;
receiving a selection of "Store" from at least one end user;
reacting to the selection of "Store" by starting application of a first stimulation to the pair of electrodes;
the first stimulation adapted to bilaterally generate action potentials in efferent motor nerves to directly promote sustained contractions of the external urethral sphincter and the external anal sphincter to preclude a release of waste;
applying the first stimulation for at least ten minutes before receiving a selection of "Void" from at least one end user;
reacting to the selection of "Void" by ceasing application of the first stimulation to the pair of electrodes;

receiving another selection of "Store" from at least one end user; and reacting to the selection of "Store" by starting application of the first stimulation to the pair of electrodes.

\* \* \* \* \*